(12) United States Patent
Vigdorchik et al.

(10) Patent No.: US 12,229,958 B2
(45) Date of Patent: *Feb. 18, 2025

(54) SYSTEM AND METHOD FOR PREDICTING A NEED FOR ARTHROPLASTY

(71) Applicant: Ortho AI LLC, New York, NY (US)

(72) Inventors: Jonathan Vigdorchik, Brooklyn, NY (US); Seth Jerabek, Pelham, NY (US); David Mayman, New York, NY (US)

(73) Assignee: Ortho AI LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/434,005

(22) Filed: Feb. 6, 2024

(65) Prior Publication Data

US 2024/0257343 A1 Aug. 1, 2024

Related U.S. Application Data

(63) Continuation of application No. 18/135,865, filed on Apr. 18, 2023, now Pat. No. 11,967,077, which is a continuation of application No. 18/103,621, filed on Jan. 31, 2023, now Pat. No. 11,669,966.

(51) Int. Cl.
*G06T 7/00* (2017.01)
*G16H 30/40* (2018.01)

(52) U.S. Cl.
CPC ........... *G06T 7/0012* (2013.01); *G16H 30/40* (2018.01); *G06T 2207/30008* (2013.01); *G06T 2207/30204* (2013.01)

(58) Field of Classification Search
CPC ............... G06T 7/0012; G06T 2200/24; G06T 2207/10081; G06T 2207/10116; G06T 2207/20081; G06T 2207/20084; G06T 2207/20101; G06T 2207/30008;
(Continued)

(56) References Cited

U.S. PATENT DOCUMENTS

| 11,645,749 B2 * | 5/2023 | Lilliestrale et al. .. G06T 7/0012 600/407 |
| 12,133,688 B2 * | 11/2024 | Chaoui .................. A61B 34/10 |

(Continued)

*Primary Examiner* — Ping Y Hsieh
*Assistant Examiner* — Jose M Torres
(74) *Attorney, Agent, or Firm* — Nicholas Pfeifer; Smith & Hopen, P. A.

(57) ABSTRACT

A system and method configured to better identify patient-specific anatomical landmarks, measure anatomical parameters and features, and predict the patient's need for surgery within a predetermined time period. In some embodiments, the system and method is configured to predict the likelihood or risk that a patient will require total hip arthroplasty. In some embodiments, the present invention includes machine learning technology Some embodiments of the present invention include a first ML machine configured to received medical images as inputs and identify anatomical landmarks as outputs; a measurement module to measure joint space width, hip dysplasia angles, and/or leg length differential; and a second ML machine configured to receive the anatomical measurements and patient demographic data as inputs and produce a risk or likelihood that the patient will require surgery within a certain time frame.

20 Claims, 38 Drawing Sheets
(33 of 38 Drawing Sheet(s) Filed in Color)

(58) Field of Classification Search
CPC .......... G06T 2207/30204; G16H 30/40; G16H 50/20; G16H 50/30; G16H 50/70
See application file for complete search history.

(56) References Cited

U.S. PATENT DOCUMENTS

2016/0228194 A1* 8/2016 Park ................ A61F 2/4657
2021/0322100 A1* 10/2021 Roche ............... A61B 90/37

* cited by examiner

SYSTEM AND METHOD FOR PREDICTING A NEED FOR ARTHROPLASTY

CROSS-REFERENCE TO RELATED APPLICATIONS

This nonprovisional application is a continuation of and claims priority to nonprovisional application Ser. No. 18/135,865, entitled "A SYSTEM AND METHOD FOR PREDICTING A NEED FOR TOTAL HIP ARTHROPLASTY," filed Apr. 18, 2023 by the same inventor(s), which is a continuation of and claims priority to nonprovisional application Ser. No. 18/103,621, now U.S. Pat. No. 11,669,966, entitled "A SYSTEM AND METHOD FOR PREDICTING A NEED FOR TOTAL HIP ARTHROPLASTY," filed Jan. 31, 2023 by the same inventor(s).

BACKGROUND OF THE INVENTION

1. Field of the Invention

This invention relates, generally, to the medical field. More specifically, it relates to a system and method for predicting a patient's need for arthroplasty.

2. Brief Description of the Prior Art

Osteoarthritis (OA) is the most common joint disease worldwide, affecting more than an estimated 240 million individuals, and is the most frequent reason for limitation of activities of daily living in adults [1]. This disability has been estimated to translate into a 20% higher age-adjusted mortality compared with individuals that do not have OA. Patients with advanced symptoms that have failed nonsurgical management trials, including physical therapy and pharmacologic analgesic agents, often choose to undergo elective total hip arthroplasty (THA). The number of annual THA procedures is estimated to increase by 174% to 572,000 procedures in the United States alone by 2030 [2]. Therefore, the ability to provide timely and accurate risk assessments for the need for future, medium- to long-term THAs among patients with hip OA is imperative. It could help better inform patient-provider decision making, particularly places where the number of orthopedic specialists is limited or their time is limited, as well as future policy decisions related to the allocation of healthcare resources to accommodate this increasing demand.

Studies across medical disciplines have developed machine learning (ML) models to predict absolute risk of clinically important events [3, 4]. However, as it pertains to patients with, or at risk for, hip OA, a long-term prognostic model for THA intervention remains elusive. Most existing studies concerning applications of predictive modeling for patients undergoing THA have focused on prediction of clinical outcomes after surgery and resource utilization metrics [5, 6], identification of implants and clinically relevant radiographic parameters [7, 8], and activity surveillance [9]. Importantly, although THA is considered an efficacious procedure for patients, as many as 7% remain unsatisfied with their surgery [10], and patients may experience complications requiring revision procedures [11-15]. Therefore, a model identifying patients at an elevated risk of eventually needing THA, particularly those at earlier stages of OA, may allow for interventions aimed at slowing disease progression and the need for THA itself. In patients at high risk, such a model may also allow for a reduction in resources spent pursuing alternative treatment options with low probabilities of success, in addition to reducing time spent directly enduring pain and dysfunction related to hip OA.

Critically, few studies have sought to leverage routine imaging obtained for the treatment of musculoskeletal pathologies [16-18]. Though integration of imaging-based data into prognostic ML models is complex, it is clinically relevant, given imaging guides treatment decisions, and is hence likely important for risk assessments. Given prior studies investigating ML to predict progression to total knee arthroplasty (TKA) [16 17], it is plausible that radiographic hip OA parameters are important considerations necessitating inclusion in a clinically useful ML model to predict THA.

The inventors designed and conducted the study described herein in subsequent sections to create an ML model integrating patient-specific demographic and radiographic measurements to predict medium- to long-term THA risk, specifically THA within ten years. As provided therein, it was determined that the combination of demographic data and radiographic measurements increased model performance compared to performance based on demographic and clinical variables alone.

In accordance with the outcomes of the study, it was determined that what is needed is an improved system and method for predicting the risk of a patient needing surgery that leverages demographic data and radiographic measurements. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a system and method for better predicting the likelihood or risk of a patient requiring a particular surgery is now met by a new, useful, and nonobvious invention.

The present invention includes a system and method for determining the risk that a patient may need arthroplasty, such as THA, within a particular time frame using ML models. The method involves acquiring a medical image and demographic data for the patient. The medical image can be an AP pelvis radiograph and the demographic data includes analgesic use and patient reported pain. Demographic data may further include but is not limited to age and hip joint stiffness.

The medical image is inputted into a first ML model that is configured to identify a plurality of anatomical landmarks, such as a portion of a femoral head and a portion of the acetabulum on a first side of the patient. The portion of the acetabulum of the first hip can include an acetabular sourcil and an outer lateral edge of the acetabulum. The portion of the acetabulum of the first hip can include an acetabular sourcil and the portion of the femoral head can include the center and perimeter of the femoral head. In some embodiments, the plurality of anatomical landmarks further includes a pelvic teardrop, an obturator foramen, a femoral greater and lesser trochanter, and an ischial tuberosity on the first side of the patient.

The method further includes acquiring quantitative values for a plurality of anatomic measurements, such as the minimum joint spacing width between the femoral head and the acetabulum. The plurality of anatomic measurements may also include a hip dysplasia angle and a leg length differential.

The anatomic measurements and the demographic data are inputted into a second machine learning model which outputs a likelihood of the patient needing THA within a certain time frame. The output may be presented to a user or the patient on a graphic user interface.

Some embodiments further include outputting, by the first ML model, a first annotated medical image with the plurality of anatomical landmarks visually identified thereon. In some embodiments, the first annotated medical image is presented with the plurality of anatomical landmarks visually identified thereon to a user on a graphic user interface and the user is provided with a plurality of tools to modify the plurality of anatomical landmarks on the first annotated medical image.

In some embodiments, the first annotated medical image is input into a feature measuring module (FMM). The FMM executes the step of acquiring quantitative values for the plurality of anatomic measurements and outputs a second annotated medical image with the plurality of anatomical measurements visually identified thereon. The second annotated medical image can be presented with the plurality of anatomical measurements visually identified thereon to a user on a graphic user interface and the user can be provided with a plurality of tools to modify the plurality of anatomical measurements on the second annotated medical image.

The present invention also includes a non-transitory computer-readable medium for determining a risk of a patient needing THA comprising instructions stored thereon, that when executed on at least one processor, cause the at least one processor to perform the steps disclosed in reference to the method of the present invention. Likewise, the present invention may be in the form of a system having at least one processor and memory including instructions that, when executed by the at least one processor, cause the system to perform the steps disclosed in reference to the method of the present invention.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which:

FIG. 9A are plots of joint space minimum. FIG. 9B are plots of joint space average. FIG. 9C are plots of Tönnis angle.

FIG. 9D are plots of ipsilateral lateral center edge angle. FIG. 9E are plots of contralateral lateral center edge angle. FIG. 9F are plots of age. FIG. 9G are plots of analgesic use. FIG. 9H are plots of ipsilateral hip pain. FIG. 9I are plots of ipsilateral knee pain. FIG. 9J are plots of ipsilateral knee stiffness.

FIG. 11A is a calibration plot (reliability curve) for the baseline model. FIG. 11B is a precision-recall curve for the baseline model. FIG. 11C is a ROC curve for the baseline model. FIG. 11D is a prediction probability histogram for the baseline model. FIG. 11E is a plot for the evaluation metric by threshold for the baseline model.

FIG. 11F is a calibration plot (reliability curve) for the radiographic model. FIG. 11G is a precision-recall curve for the radiographic model. FIG. 11H is a ROC curve for the radiographic model. FIG. 11I is a prediction probability histogram for the radiographic model. FIG. 11J is a plot for the evaluation metric by threshold for the radiographic model.

FIG. 11K is a calibration plot (reliability curve) for the combined model. FIG. 11L is a precision-recall curve for the combined model. FIG. 11M is a ROC curve for the combined model. FIG. 11N is a prediction probability histogram for the combined model. FIG. 11O is a plot for the evaluation metric by threshold for the combined model.

DETAILED DESCRIPTION OF THE INVENTION

Figure 1:
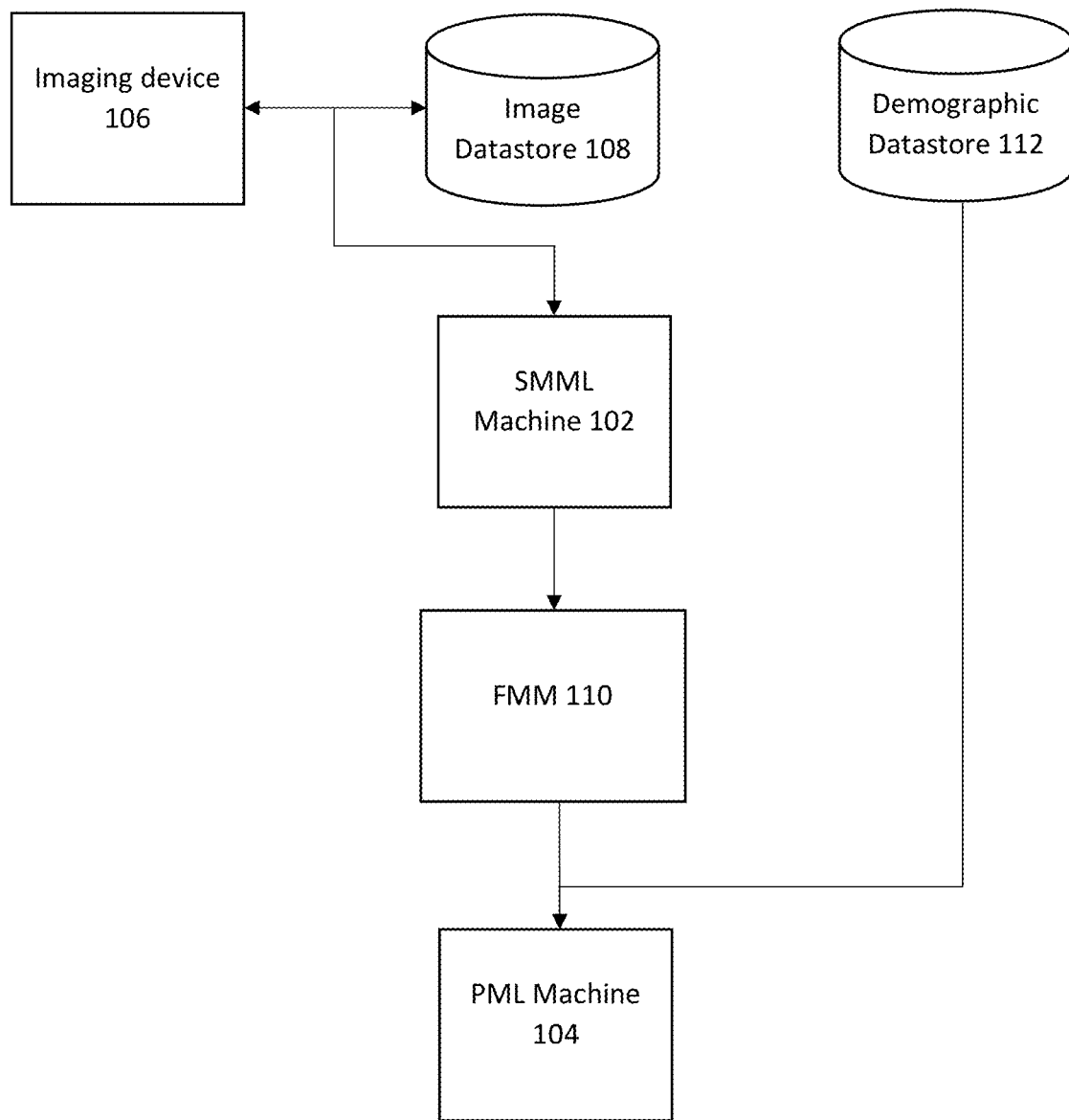
FIG. 1 is a block diagram of an embodiment of the present invention.

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

In the following description, for the purposes of explanation, numerous specific details are set forth in order to provide a thorough understanding of embodiments of the present technology. It will be apparent, however, to one skilled in the art that embodiments of the present technology may be practiced without some of these specific details. The techniques introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions which may be used to program a computer (or other electronic devices) to perform a process on one or more local devices or through a web-based application. The machine-readable medium may include, but is not limited to, floppy diskettes, optical disks, compacts disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions.

The phrases "in some embodiments," "according to some embodiments," "in the embodiments shown," "in other embodiments," and the like generally mean the particular feature, structure, or characteristic following the phrase is included in at least one implementation. In addition, such phrases do not necessarily refer to the same embodiments or different embodiments.

As used herein, the term "medical images" refers to images depicting a patient's anatomy, including but not limited to radiographic and x-ray images. Alternative types of medical images known to a person of ordinary skill in the art may be used. The present invention may be adapted to receive the image files in any format including, but not limited to .png, .bmp, .jpg, .heic, and DICOM format. Some embodiments of the present invention include imaging devices configured to capture the medical images of the patient. Alternatively, the system is configured to access one or more databases to retrieve the required medical images, such as a hospital or doctor office PACS systems.

Referring now to the specifics of the present invention, some embodiments, include one or more computer systems having a memory, a user interface with a visual display (also referred to as a "graphic user interface" or "GUI"), and a processor for executing a program performing at least the steps described herein. In some embodiments, the present invention is a computer executable method or is a method embodied in software for executing the steps described herein. Further explanation of the hardware and software can be found in the Hardware and software infrastructure examples section below.

The present invention includes a system and method configured to better identify patient-specific anatomical landmarks, measure anatomical parameters and features (e.g., spacing, angles, and length), and predict the patient's need for surgery within a predetermined time period. In some embodiments, the system and method are configured to predict the likelihood or risk that a patient will require THA. In some embodiments, the system and method are configured to predict the likelihood or risk that a patient will require THA in the next 10 years.

In some embodiments, the present invention includes machine learning technology (e.g., a ML machine or an ML model). Such embodiments include one or more trained ML machines as will be explained in greater detail herein. The ML machines are trained or acquired as a pre-trained machines.

ML technology generally refers to computer-based technology that is configured to learn from data. ML is based on the idea that after learning, machines use the learning to make predictions or decisions without being explicitly programmed to perform the task.

Typically, ML involves a computer program that is designed to create an ML model, comprised of one or more algorithms. The algorithms are configured to produce an output based on input data. Once trained, the ML machine will use the ML model to receive inputs and produce a desired output. ML models include but are not limited to neural networks, decision trees, support vector machines, and k-means clustering.

During training, the ML machines receive specific inputs through training data and manipulate the ML model until the ML model produces correct outputs at a certain threshold rate. Once this threshold is reached, the ML machine is deemed to be a trained ML machine. Training may be performed using any known methods and approaches.

In order for a particular ML machine to be useful for a specific purpose, it must be trained to produce a particular output from a certain type of input parameter. As will be explained in greater detail below, some embodiments of the present invention include (1) a first ML machine configured to receive medical images as inputs and identify anatomical landmarks as outputs, which may be in form of annotated medical images and (2) a second ML machine configured to receive anatomical measurements and patient demographic data as inputs and produce a risk or likelihood that the patient will require surgery within a certain time frame.

While some embodiments of the present invention use a computer system, including one or more ML machines to automatically perform one or more of the various steps described herein, some embodiments may include alternative or additional user actions. For example, the various steps described herein may be reviewed by a user for accuracy and acceptability. In addition, the results following the various steps described may be visually displayed on a GUI to provide the user with the ability to review and, in some embodiments, modify the results. Thus, the user is also provided with controls to remove, change, or add medical images, anatomical landmarks, features, measurements, etc.

In some embodiments, the system displays to a user the results after one or more steps in each of the different processes described herein. In some embodiments, the system displays to a user the results after every step in each of the different processes described herein.

Referring now to FIG. 1, an embodiment of the system includes a first ML machine and a second ML machine. The first ML machine is a segmentation ML machine ("SML") 102. The second ML machine is a prediction ML machine ("PML") 104.

SML 102 is configured to receive medical images as inputs. To do so, SML 102 may be in wired or wireless communication with imaging device 106 (and/or its related computing device) and/or imaging datastore 108. Imaging device 106 may be any device configured to capture medical images of a patient's anatomy. Likewise, imaging datastore 108 may be any datastore configured to store medical images. In some embodiments, the medical images are AP pelvis radiographs as is standard in the industry. However, medical images may be any type of image that provides a picture of the pelvic anatomy.

In some embodiments, SML 102 is a trained ML machine configured to identify anatomical landmarks/features of interest from the input medical images. SML 102 may include a single ML model to identify each of the anatomical landmarks/features or may include a plurality of different ML models with each designed to identify one or more of the anatomical landmarks/features. Non-limiting examples of these landmarks include all or portions of the femoral head and acetabular sourcil, which are used for measuring joint space width (JSW); femoral head, acetabular sourcil, pelvic teardrop, and obturator foramen which are used for measuring hip dysplasia angles (HDA); and femoral head, pelvic teardrop, obturator foramen, femoral trochanters, and ischial tuberosity which are used for measuring LLD. Table 2 herein provides a list of the various anatomical landmarks that SML 102 may be configured to identify.

Regardless of the number of models used, SML 102 is designed to receive medical images as input and output annotated medical images with the anatomical landmarks/features of interest identified thereon. To properly and consistently identify anatomy of interest, SML 102 is preferably trained on medical images to identify the anatomical landmarks and features of interest. Details regarding identifying anatomy of interest during training and inference are described in the experimentation section herein.

Figure 4A:
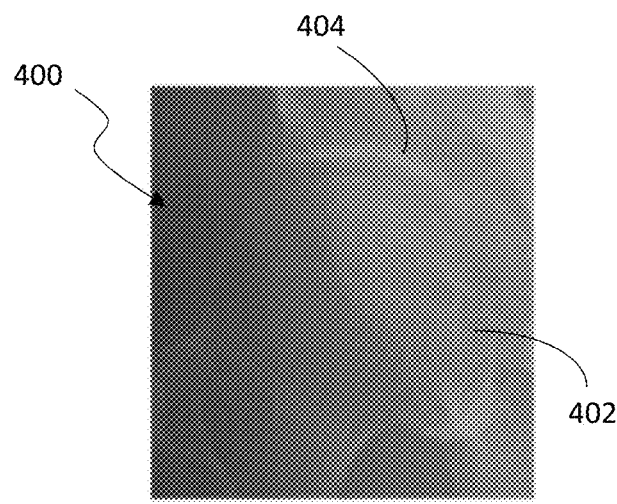
FIG. 4A is an exemplary annotated medical image identifying the femoral head and the acetabular sourcil.
Figure 4B:
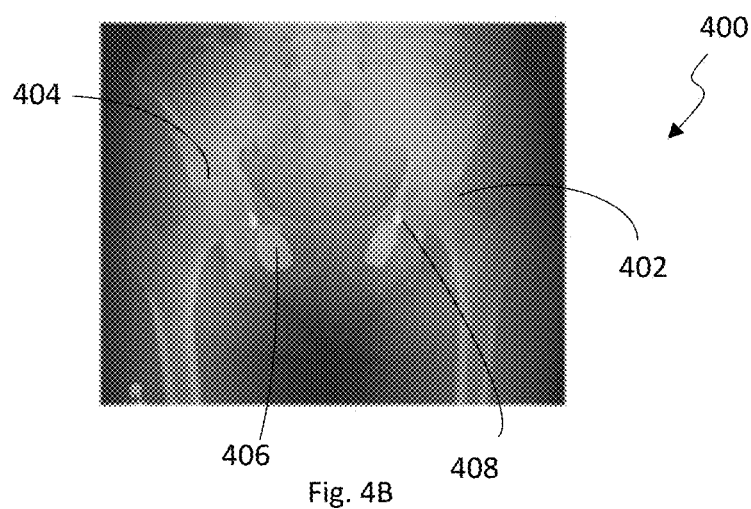
FIG. 4B is an exemplary annotated medical image identifying the femoral head, acetabular sourcil, pelvic teardrop, and obturator foramen.
Figure 4C:
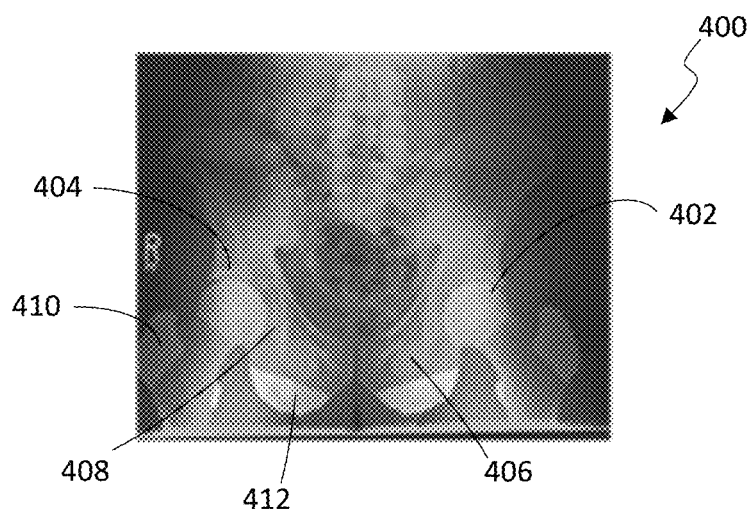
FIG. 4C is an exemplary annotated medical image identifying the femoral head, acetabular sourcil, pelvic teardrop, obturator foramen, femoral trochanters, and ischial tuberosity.

The output annotated medical images from SML 102 may include one or more visual indicia to identify the various anatomical features of interest. Non-limiting examples include points, lines, highlighted regions, outlines, overlays, etc. Some examples are provided in FIG. 4. Specifically, FIG. 4A exemplifies the identification of the femoral head 402 and the acetabular sourcil 404 on an annotated medical image. FIG. 4B exemplifies the identification of the femoral head 402, the acetabular sourcil 404, pelvic teardrop 406, and obturator foramen 408 on an annotated medical image. FIG. 4C exemplifies the identification of the femoral head 402, the acetabular sourcil 404, pelvic teardrop 406, obturator foramen 408, femoral trochanters 410, and ischial tuberosity 412 on an annotated medical image.

In some embodiments, SML 102 is configured to automatically identify, for at least the hip of interest, the most lateral point of sourcil, the most medial point of sourcil, and/or the average of some or all possible radians, which are used to the sourcil to measure JSW. Likewise, SML 102 is configured to automatically identify corresponding points on the femoral head that are vertically aligned with the same sourcil points.

In some embodiments, SML 102 is configured to automatically identify, for at least the hip of interest, the bilateral pelvic teardrops, the most medial and/or lateral edges of sourcil, the center of the femoral head, the longitudinal axis of the pelvis, and/or the most inferior margin of the pelvic teardrop, which are used to measure HDA.

In some embodiments, SML 102 is configured to automatically identify, for each half of the patient's body, all or portions of the pelvic teardrops, greater trochanters, lesser trochanters, femoral heads, the top obturator foramens, the bottom obturator foramens, and/or ischial tuberosities to measure LLD.

Some embodiments of SML 102 include an additional, fourth ML model used to determine the presence of an implant on the contralateral side. As such, SML 102 can identify which hip to annotate with the various features. As will be explained in the experimentation section, these values were compared against the variable measuring presence of an implant on the contralateral hip, obtaining 100% accuracy among observations with this variable available in the training data (Table 5).

SML 102 outputs the annotated images with the identified anatomical landmarks thereon and sends the annotated images to feature measuring module (FMM) 110. FMM 110 can be software, a computer device, and/or ML machine configured to recognize the identified anatomical landmarks/features of interest in the annotated images provided from SML 102 and measure anatomical features (e.g., distances and/or angles) using one or more measurements for each feature. The measured anatomical features include each of JSW, HDA, and LLD. Some embodiments include taking the measurements for JSW. Some embodiments include taking the measurements for HDA. Some embodiments include taking the measurements for LLD. Some embodiments include taking the measurements for any combination of two of JSW, HDA, and LLD.

Table 2 below provides a list of the various measurements that can be used to measure JSW, HDA, and LLD. In some embodiments, FMM 110 uses all 26 radiographic measurements. In some embodiments, FMM 110 uses a subset of the listed radiographic measurements to measure JSW, HDA, and LLD.

In some embodiments, JSW measurements include but are not limited to joint space width minimum, maximum, average, lateral and/or medial sourcil measurements. In some embodiments, FMM 110 calculates at least the minimum space between the inferior contour of the acetabulum (sourcil) and the femoral head to calculate JSW.

In some embodiments, HDA measurements include but are not limited to Tönnis angle, Sharp's angle, and/or lateral center-edge angle. In some embodiments, FMM 110 calculates at least the lateral center edge angle—the angle subtended by a line from the center of the femoral head to the lateral sourcil and a line parallel to the longitudinal axis of the pelvis—to calculate HDA. In some embodiments, LLD measurements include comparative contralateral measurements relative to various anatomical landmarks, including femoral and pelvic landmarks.

In some embodiments, SML 102 is configured to measure the three groups of radiographic features instead of FMM 110. To do so, SML 102 is trained to take all or a subset of the measurements identified in Table 2.

As previously noted, the system of the present invention includes PML 104. PML 104 is configured to receive as inputs the patient demographic data and also the output data from FMM 110, or SML 102 when SML 102 calculates the measurements. Thus, PML 104 is in wired or wireless communication with FMM 110 (and/or SML 102) and demographic datastore 112.

Demographic datastore 112 may be any datastore known to a person of ordinary skill in the art. The demographic data includes whether or not the patient is in pain (or a level of pain of a scale such as 1-10), analgesic use (could be used within a predetermined time frame), and/or age. This data is provided on a scale of quantitative values or on a binary scale. Additional demographic data may include BMI, sex, height, race, ethnicity, income, and/or education. In some embodiments, PML 104 is configured to receive a subset of the patient's demographic data. For example, PML 104 may receive only the quantitative representation of the patient's reported pain/pain level.

Demographic datastore 112 may be comprised of one or more electronic medical records systems/databases or may automatically comb these systems to retrieve patient data. In addition, demographic datastore 112 may receive information directly from the patient or from the medical provider.

Output data from FMM 110 (and/or SML 102) and patient demographic data is in the form of quantitative measurements. Thus, PML 104 is configured to receive such data and then output a prediction of the likelihood of the patient needing surgery within a predefined timeframe. In some embodiments, the surgery is THA.

PML 104 uses the input data and outputs a prediction of the likelihood of the patient needing surgery within a predefined timeframe. The prediction can be in the form of a percent likelihood, a yes/no answer, or another alternative answer to inform the patient and medical provider. In some embodiments, the time frame is 10 years. In some embodiments, the time frame may be more or less than 10 years. For example, the time frame could be within the next year, within 5 years, within 15 years, or within 20 years. Alternative time frames could be used as well.

In some embodiments, PML 104 is a trained ML machine. PML 104 may include a single ML model or may include a plurality of different ML models with each designed to identify one or more of the anatomical measurements and the demographic data to predict the risk/likelihood of the patient needing surgery within a predefined timeframe. To properly and consistently predict risk, PML 104 is preferably trained on similar data with associated ground truths. Details regarding training and inference of PML 104 are described in the experimentation section herein.

Figure 2:
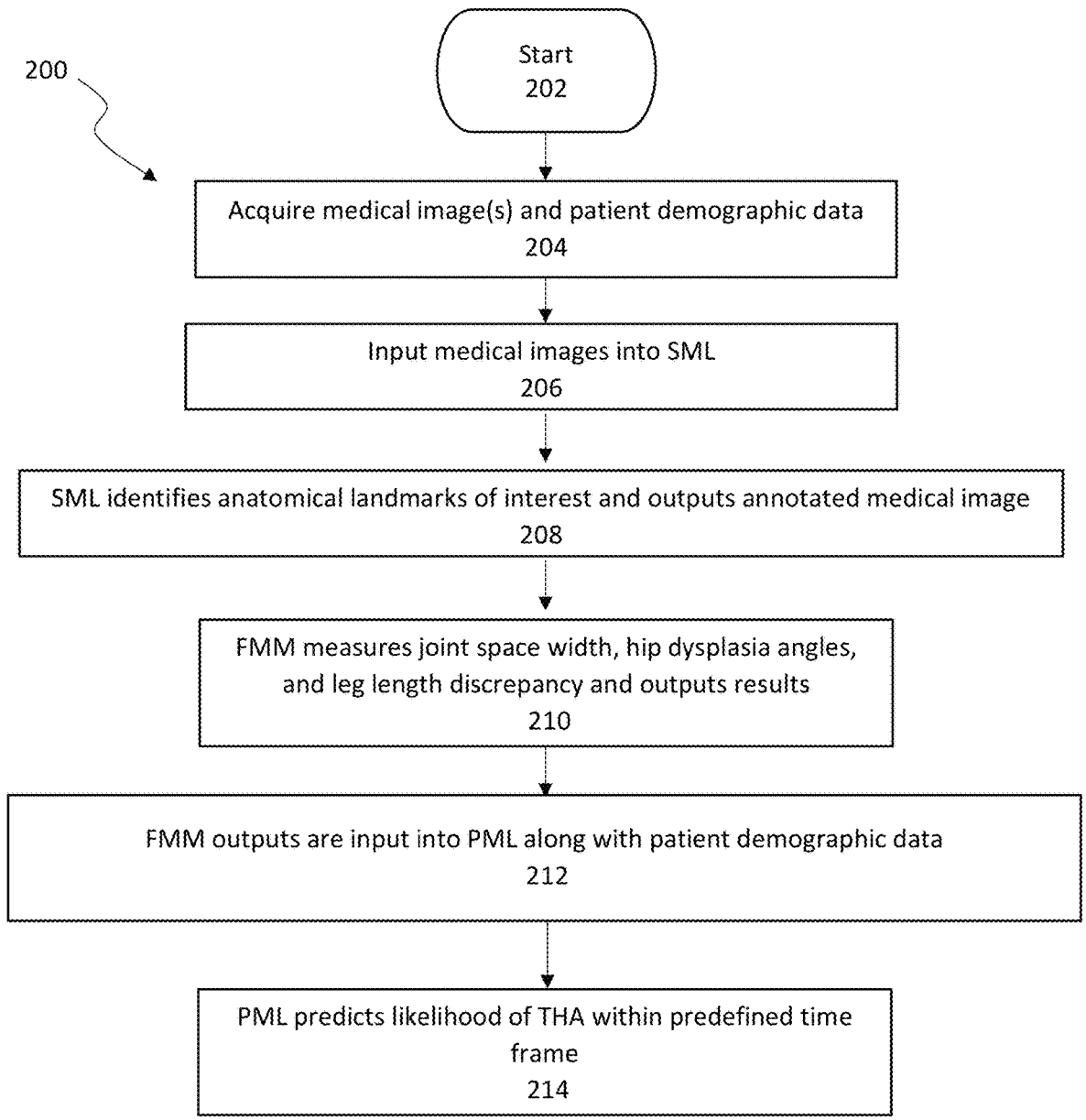
FIG. 2 is a flowchart of an embodiment of the present invention.

Referring now to FIG. 2, an embodiment of the present invention includes method 200, in which medical image(s) and patient demographic data are acquired at step 204. As previously explained, the medical images can be acquired directly from imaging device 106 and/or from a corresponding image datastore 108. The medical images are preferably AP images of the pelvis, but could be alternative views of the pelvis and femur.

The patient demographic data is also acquired as exemplified in step 204. Patient demographic data may be acquired from demographic datastore 112 or directly input through a GUI.

Figure 3:
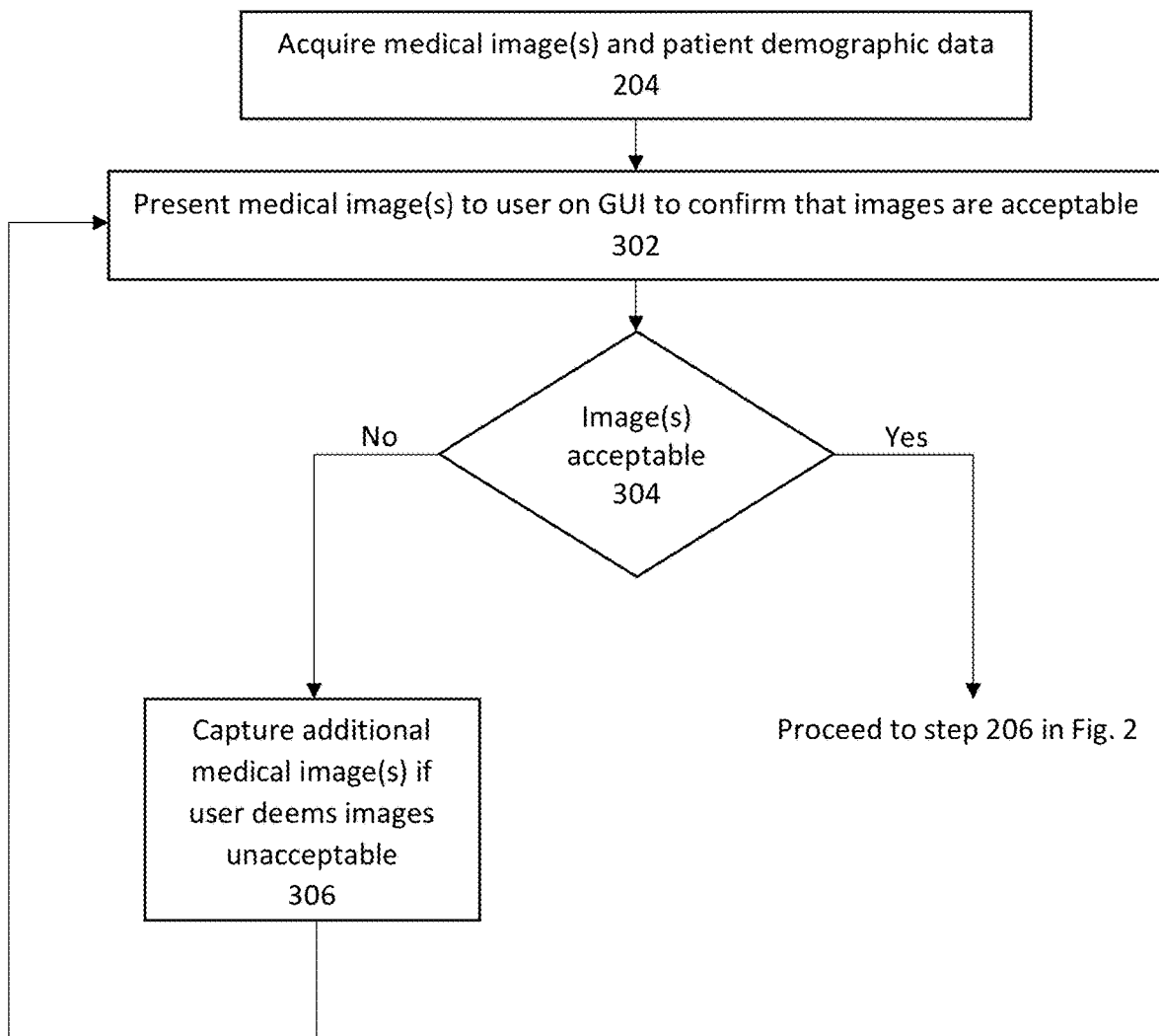
FIG. 3 is a flowchart of additional steps included in some embodiments of the present invention.

Some embodiments, as exemplified in FIG. 3, include additional steps 302-306. At step 302, the medical images are presented to a user, such as a patient or a medical professional, prior to inputting the images into SML 102. The user is given an opportunity to discard or exchange any images for alternative images in case the image or set of images are inadequate at step 304. If deemed inadequate, additional medical image(s) are captured at step 306. The new image(s) are then presented to the user at step 302. This loop comprised of steps 302-306 continues until the user determines that the images are acceptable.

Referring back to FIG. 2, at step 206, one or more medical images for the patient are input into SML 102 as inputs. SML 102 then automatically identifies anatomical landmarks/features of interest at step 208 based on its ML model. As previously explained, non-limiting examples of the identified anatomical landmarks include the femoral head 402, acetabular sourcil 404, pelvic teardrop 406, obturator foramen 408, femoral trochanters 410, and ischial tuberosity 412 as shown in FIG. 4.

Figure 5:
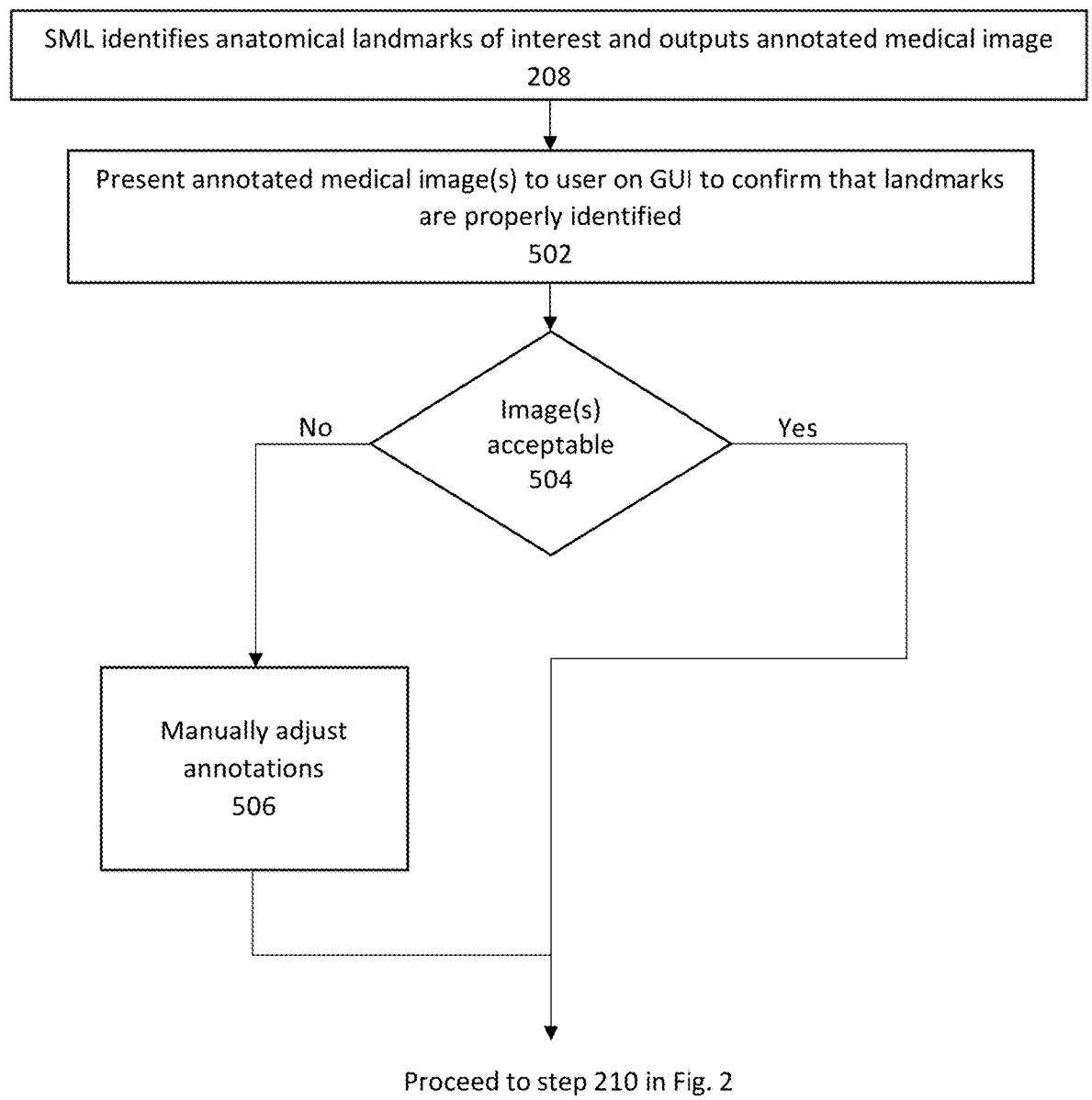
FIG. 5 is a flowchart of additional steps included in some embodiments of the present invention.

Referring now to FIG. 5, some embodiments include additional steps for presenting the SML-identified anatomical landmarks to a user on a GUI prior to executing the subsequent steps in FIG. 2. These additional steps include 502-506. At step 502, the annotated medical images are presented to a user for review to determine whether SML 102 properly identified each of the anatomical features of interest (see FIG. 4 for examples of annotated medical images). At step 504, the medical profession indicates whether SML 102 properly identified each of the anatomical features of interest. If SML 102 incorrectly identified one or more of the anatomical features or the annotation(s) need to be adjusted, the user is provided with a series of tools on the GUI to adjust, delete, and/or add annotations at step 506. If the user determines that the annotations are correct and do not need to be adjusted in any way, the annotated images are sent to FMM 110.

Referring back to FIG. 2, the annotated medical images are provided to FMM 110. FMM 110 measures the anatomical features in the annotated medical images and outputs the quantitative results at step 210. As previously explained, these measurements can include JSW, HDA, and/or LLD. In some embodiments, SML 102 executed step 210 instead of FMM 110.

Figure 6:
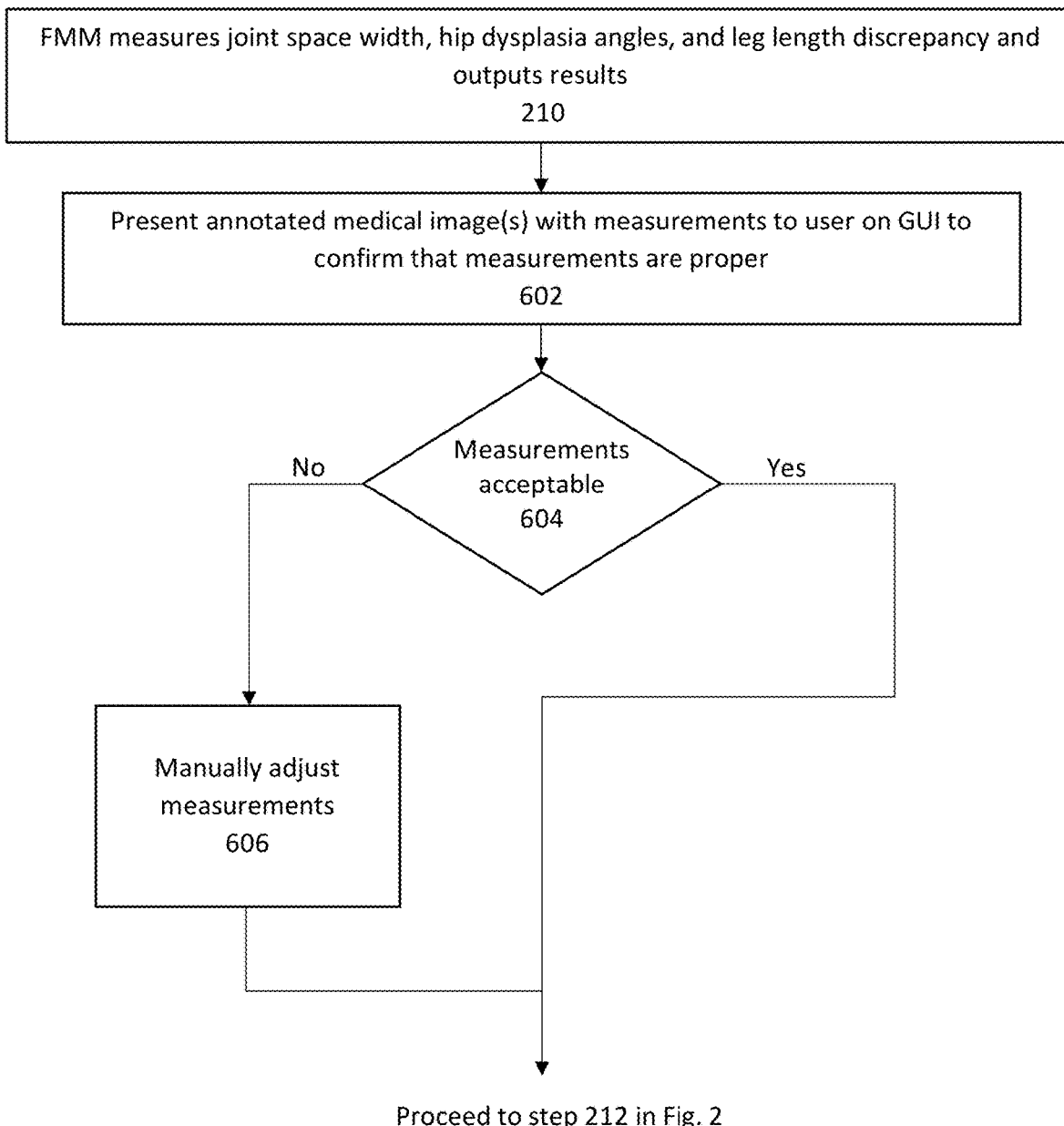
FIG. 6 is a flowchart of additional steps included in some embodiments of the present invention.

As provided in FIG. 6, some embodiments include additional steps 602-606 for confirming that the measurements output by FMM 110 are proper. At step 602, the annotated medical image(s) with measurements are presented to a user to determine if the measurements output by FMM 110 are proper. In some embodiments, the different measurements for JSW, HDA, and LLD are displayed separately to improve clarity, however, the measurements could all be shown on the same annotated image. In addition, these images may include the previous annotations corresponding to the identification of landmarks or may include said previous annotations removed as exemplified in FIG. 7.

Figure 7A:
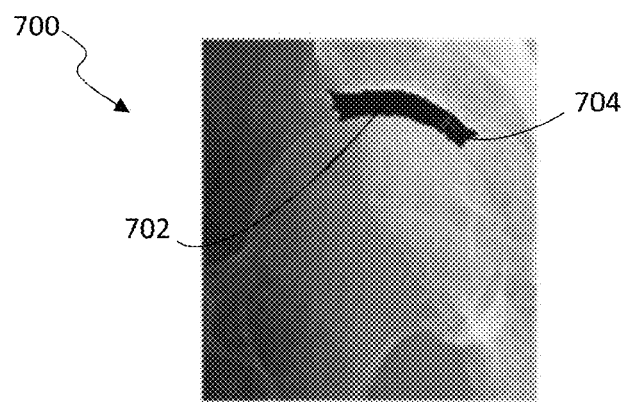
FIG. 7A is an exemplary annotated medical image having measurements of JSW.

As provided in FIG. 7A, for assessment of JSW measurements, the user is presented with annotated image 700 depicting a close-up view of the hip joint. Specifically, image 700 includes joint space 702 highlighted with the minimal spacing measurement 704 highlighted in red.

Figure 7B:
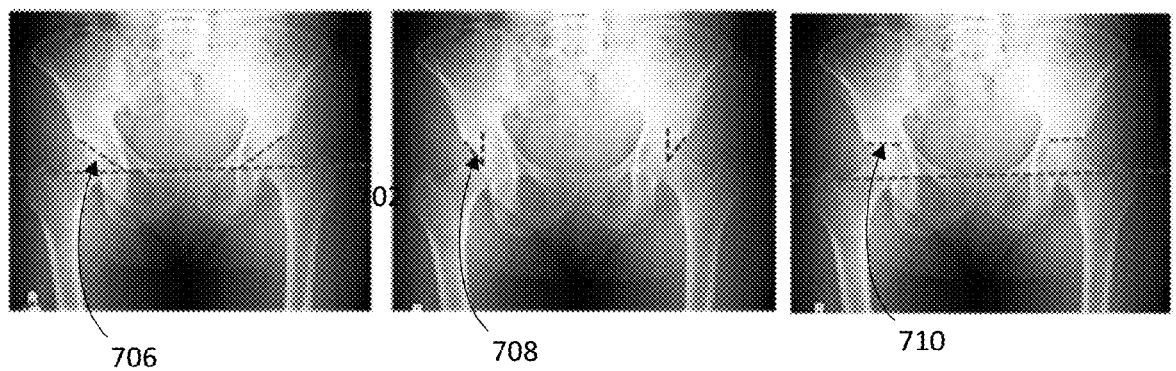
FIG. 7B is a collection of three annotated medical images having measurements of HDA.

As provided in FIG. 7B, for assessment of HDA measurements, the user is presented with one or more annotated images depicting points, lines, and angles for measuring HDA. For example, the far left annotated image shows annotated lines in the form of the Sharp's angle 706—the acute angle measured between the projection of the horizontal teardrop line and the line connecting the teardrop to the lateral acetabulum. The middle image in FIG. 7B is an example image provided to the user in which the lateral center-edge angle 708—a radiographic measurement of the superolateral femoral head bony coverage by the acetabulum—is displayed on the annotated medical image. The right image in FIG. 7B is an example image provided to the user in which the Tönnis angle 710—the measure of the acetabular inclination.

Figure 7C:
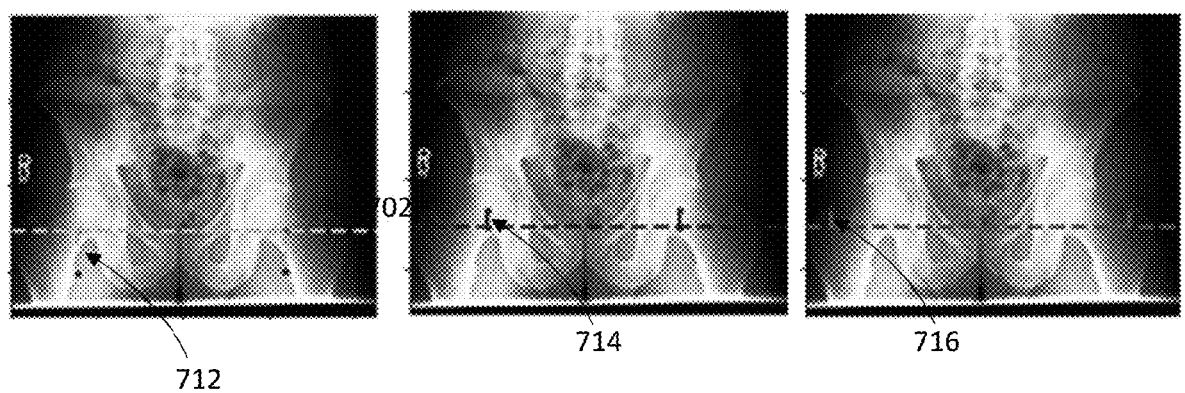
FIG. 7C is a collection of three annotated medical images having measurements of LLD.

Similarly, FIG. 7C shows three annotated images. Again, more or less annotated images can be presented to the medical profession to determine whether FMM 110 executed the proper measurements to assess LLD. The far left image is an exemplary image of the measurement line 712 between the teardrop and the lesser trochanter; the middle image is an exemplary image of the measurement line 714 between the teardrop and the center of the femoral head; the right image is an exemplary image of the measurement line 716 between the teardrop and the greater trochanter.

Referring back to FIG. 6, at step 604, the medical profession indicates whether FMM 110 properly measured each of the anatomical features of interest. If any of the measurements are improper or need to be adjusted, the user is provided with a series of tools on the GUI to adjust, delete, and/or add measurements at step 606. If the user determines that the annotations are correct and do not need to be adjusted in any way, the method continues to step 212.

Referring back to FIG. 2, the novel method includes inputting the FMM outputs and demographic data into PML 104. PML 214 uses these inputs and its ML model to predict the likelihood of the patient needing surgery, e.g., THA, within a predetermined time frame, e.g., 10 years. The prediction is outputted to the user and/or patient on a GUI or through an automated message.

In some embodiments, SML 102 and PML 104 are a single ML machine configured to use specific ML models to achieve the desired outputs from the described inputs. In some embodiments, SML 102 and FMM 110 are a single ML machine configured to use specific ML models to achieve the desired outputs from the described inputs. In some embodiments, PML 104 and FMM 110 are a single ML machine configured to use specific ML models to achieve the desired outputs from the described inputs. In some embodiments, SML 102, PML 104, and FMM 110 are a single ML machine configured to use specific ML models to achieve the desired outputs from the described inputs. Furthermore, each of SML 102, PML 104, and FMM 110 may be comprised of a statistical regression modelling (ML or non-ML) approach to perform their specific tasks as described herein.

Experimentation

Data Sources and Participants

Data was acquired from a multi-center, publicly available dataset of almost 5,000 patients for the study of OA progression and outcomes focused on the knee. However, in addition to demographic and clinical information, the study collected patient data concerning hip OA, including baseline visit anteroposterior (AP) pelvis radiographs and THA outcomes.

Baseline Features: Orthopedic Data

To enumerate features likely to predict THA, a literature review on machine learning models using a database of orthopedic images and data, such as those predicting total knee arthroplasty, total hip arthroplasty, or osteoarthritis progression was conducted [16, 17, 19, 20]. Predictive features were included based on relevance to the OA medical workup and potential surgical intervention (e.g., patient demographics, medical history, social history, surgical history, family history, functional assessment). Furthermore, for predictive features depending on laterality (e.g., left versus right hip pain), both an ipsilateral feature (e.g., left hip pain for the left hip) and contralateral feature (e.g., right hip pain for the left hip) were included. There were 110 total baseline demographic and clinical features (See Table 1 below). Outcome of THA for a given hip was defined as having a follow-up hip-specific replacement date after enrollment. This ensured that hips with a replacement at baseline were not counted as cases.

TABLE 1

All variables included from the database for model training

| Category | Variables | References |
|---|---|---|
| Demographics | Age | Tolpadi et al. |
| | BMI | (2020) [17] |
| | Sex | Liu et al. |
| | Height | (2022) [16] |
| | Race | |
| | Ethnicity | |
| | Income | |
| | Education | |
| Medical History | SF-12-mental health | Tolpadi et al. |
| | SF-12-physical health | (2020) [17] |
| | SF-12-general health | Liu et al. |
| | CES-D-depression | (2022) [16] |
| | Previous hip pain* | |
| | Previous arthritis (rheumatoid) | |
| | Morning stiffness | |
| | Heberden nodes fingertips | |
| | Heberden nodes joints | |
| | Osteoarthritis diagnosis (back, knee, hip, hand, other joint) | |
| | Low back pain | |
| | Low back pain effect on activities | |
| | Low back pain location | |
| | Blood pressure (systolic and diastolic) | |
| | Comorbidity score | |
| | History of asthma | |
| | History of COPD | |
| | History of diabetes | |
| | History of rheumatoid arthritis | |
| | History of stroke | |
| | History of diabetes | |
| | History of heart attack (and treatment) | |
| | Analgesic usage (past 30 days) | |
| | Narcotic usage (past 30 days) | |

TABLE 1-continued

All variables included from the database for model training

| Category | Variables | References |
|---|---|---|
| | NSAID usage (past 30 days) | |
| | Seeing doctor for knee arthritis | |
| Social History | Employment | Tolpadi et al. |
| | Current work for pay | (2020) [17] |
| | Health care coverage | Hartnett et al. |
| | Marital status | (2022) [20] |
| | Smoking status and nicotine usage | Schafer et al. |
| | Alcohol usage | (2010) [50] |
| | Physical activity score | |
| Surgical History | Previous hip surgery * | Tolpadi et al. |
| | Previous hip surgery reason (hip fracture) * | (2020) [17] |
| | Previous hip surgery reason (osteoarthritis) * | |
| Family History | Hip surgery | Bukulmez et al. |
| | Knee surgery | (2006) [51] |
| Functional Assessment | WOMAC total score* | Tolpadi et al. |
| | WOMAC disability score* | (2020) [17] |
| | WOMAC pain score* | Liu et al. |
| | WOMAC stiffness score* | (2022) [16] |
| | KOOS pain score* | |
| | KOOS symptom score* | |
| | Patient ability to climb stairs | |
| | Patient ability to kneel | |
| | Patient ability to squat | |
| | Patient ability to lift | |
| Knee Specific Parameters | Current knee pain* | Tolpadi et al. |
| | Knee pain in the past 30 days* | (2020) [17] |
| | Knee baseline symptom status* | Liu et al. |
| | Knee baseline symptomatic OA status* | (2022) [16] |
| | Knee pain frequency* | |
| | Knee KL grade* | |
| | History of meniscectomy* | |
| | History of ligament repair* | |
| | History of injury limiting functionality* | |
| | Ability to kneel and frequency | |
| | Ability to squatting and frequency | |
| | Previous knee surgery | |
| | Previous arthroscopy treatment | |
| | Previous hyaluronic acid injection * | |
| | Previous knee steroid injection | |

*ipsilateral and contralateral variables

Hip Radiographic Features: Deep Learning (U-Net) Segmentation and Measurements Radiographic parameters from AP pelvis radiographs were not measured in the data. Based on literature, 3 groups of radiographic measurements were determined to be relevant to OA and OA progression: (1) joint space width (joint space width minimum, maximum, average, lateral and medial sourcil measurements), (2) hip dysplasia angles (Tönnis angle, Sharp's angle, lateral center-edge angle), and (3) leg length discrepancy [21-24]. The descriptors are provided in Table 2 below.

TABLE 2

Hip radiograph measurement descriptors

| Measurement | Number of measurements | Description | Reference |
|---|---|---|---|
| Joint Space Width (JSW) * | 8 | Distance between the inferior contour of the acetabulum (sourcil) and the femoral head Minimum space Most lateral point of sourcil Most medial point of sourcil Average of all possible radians | Mannava et al. (2017) [23] Goker et al. (2000) [52] |
| Tönnis Angle* (Dysplasia) | 2 | Angle subtended by horizontal line drawn between bilateral teardrops and line from most medial and lateral edges of sourcil | Mannava et al. [23] |
| Lateral Center Edge Angle (Dysplasia) * | 2 | Angle subtended by line from center of the femoral head to the lateral sourcil and line parallel to the longitudinal axis of the pelvis | Mannava et al. [23] |
| Sharp's Angle* (Dysplasia) | 2 | Angle subtended by line from most inferior margin of the teardrop to the lateral sourcil edge and line connecting the bilateral teardrops | Mannava et al. [23] |
| Leg Length Discrepancy (LLD) | 12 | Absolute difference in leg length using various femoral and pelvic landmarks: Teardrop and greater trochanter; Teardrop and lesser trochanter; Teardrop and femoral head; Top obturator foramen and greater trochanter; Top obturator foramen and lesser trochanter; Top obturator foramen and femoral head; Bottom obturator foramen and greater trochanter; Bottom obturator foramen and lesser trochanter; Bottom obturator foramen and femoral head; Ischial tuberosity and greater trochanter; Ischial tuberosity and lesser trochanter; Ischial tuberosity and femoral head | Flecher et al. (2016) [53] |
| Contralateral implant* | Y/N | Determination of existing implant on either side of the pelvis | |

*Including ipsilateral and contralateral variables

Previous work has applied deep learning to automatically measure radiographic parameters on orthopedic images [7, 25]. However, these studies did not measure the precise parameters identified herein. The current study therefore created deep learning algorithms (i.e., ML models) based on U-Net architectures to identify (segment) anatomical landmarks from which 26 radiographic measurements were derived. For details, see the measurement outcomes in Table 3 below.

TABLE 3

Deep learning hip radiograph measurement outcomes

| Measurement | Mean (SD) | Bounds | Excluded hips |
|---|---|---|---|
| Joint Space Width Minimum (mm) | 3.27 (0.68) | 0 to 20 mm | 51 without CNN outputs 2 out of bounds |
| Joint Space Width Lateral (mm) | 6.22 (1.15) | 0 to 20 mm | 51 without CNN outputs 2 out of bounds |
| Joint Space Width Medial (mm) | 4.90 (1.17) | 0 to 20 mm | 51 without CNN outputs 8 out of bounds |
| Joint Space Width Average (mm) | 4.44 (0.74) | 0 to 20 mm | 51 without CNN outputs 4 out of bounds |

TABLE 3-continued

Deep learning hip radiograph measurement outcomes

| Measurement | Mean (SD) | Bounds | Excluded hips |
|---|---|---|---|
| Lateral Center Edge Angle (mm) | 31.2 (2.35) | 0 to 70 degrees | 393 without CNN outputs<br>0 out of bounds |
| Sharp's Angle (degrees) | 37.8 (4.02) | 5 to 70 degrees | 59 without CNN outputs<br>12 out of bounds |
| Tönnis Angle (degrees) | 4.94 (5.34) | −30 to 40 degrees | 59 without CNN outputs<br>0 out of bounds |
| LLD: Teardrop-Lesser Trochanter (mm) | 4.66 (3.84) | n/a | 1,132 without CNN outputs<br>0 out of bounds |
| LLD: Teardrop-Greater Trochanter (mm) | 5.84 (6.45) | n/a | 1,132 without CNN outputs<br>0 out of bounds |
| LLD: Teardrop-Femoral Head Center (mm) | 2.82 (2.78) | n/a | 1,132 without CNN outputs<br>0 out of bounds |
| LLD: Top Obturator Foramen-Lesser Trochanter (mm) | 4.82 (4.08) | n/a | 1,132 without CNN outputs<br>0 out of bounds |
| LLD: Top Obturator Foramen-Greater Trochanter (mm) | 5.59 (6.44) | n/a | 1,132 without CNN outputs<br>0 out of bounds |
| LLD: Top Obturator Foramen-Femoral Head (mm) | 3.27 (3.03) | n/a | 1,132 without CNN outputs<br>0 out of bounds |
| LLD: Bottom Obturator Foramen-Lesser Trochanter (mm) | 4.69 (3.81) | n/a | 1,132 without CNN outputs<br>0 out of bounds |
| LLD: Bottom Obturator Foramen-Greater Trochanter (mm) | 6.47 (6.87) | n/a | 1,132 without CNN outputs<br>0 out of bounds |
| LLD: Bottom Obturator Foramen-Femoral Head (mm) | 2.97 (2.76) | n/a | 1,132 without CNN outputs<br>0 out of bounds |
| LLD: Ischial Tuberosity-Lesser Trochanter (mm) | 5.35 (4.21) | n/a | 1,132 without CNN outputs<br>0 out of bounds |
| LLD: Ischial Tuberosity-Greater Trochanter (mm) | 7.72 (7.73) | n/a | 1,132 without CNN outputs<br>0 out of bounds |
| LLD: Ischial Tuberosity-Femoral Head (mm) | 3.39 (3.48) | n/a | 1,132 without CNN outputs<br>0 out of bounds |

*Without CNN outputs indicates that landmarks on radiographs were not present to adequately assess the measurement Statistical Analysis: GA2M Modeling To predict ten-year incidence of THA, three machine learning models were trained with different predictive feature sets: 1) baseline model with demographic and clinical variables, 2) radiographic model with deep learning-derived radiographic variables, and 3) combined model with demographic, clinical, and deep learning-derived radiographic variables. Training and testing cohorts were formed by randomly splitting the dataset 80:20 using all 4,796 patients and 9,592 hips, where 80% were used for training, and 20% for testing. Although each hip was considered a separate case, cohorts were split at the patient level to prevent data leakage. If a patient's left hip was in the training cohort, the right hip was also in the training cohort. The same training and testing cohorts were used in the three models to compare performance. We leveraged General Additive Models with Pairwise Interactions (GA2Ms) [26], which include one-dimensional components for each feature, as well as a smaller number of two-dimensional components, where we specify the number of such interaction features but not precisely which interactions to include. These pairwise components are selected by the model, which automatically ranks the top pairwise features among all possible pairs. Importantly, GA2Ms do not impose linear functional forms and are fully interpretable (i.e., "glass box"). This is in contrast with linear models like logistic regression, in which each feature has a single coefficient representing its contribution to the model's prediction. These models have been used in healthcare applications, have performance comparable to other standard models, and produce fully transparent visual explanations of model behavior [27]. Model performance was assessed using the area under the receiver operating characteristic curve (AUROC) and area under the precision recall curve (AUPRC).

Each feature in a GA2M has an entire (potentially non-linear) graph representing how the model assigns risk along the feature's domain; pairwise features can be represented by similar heatmaps defined along the domains of both variables. These were inspected for discontinuities in predicted risk to uncover potential thresholds indicating particularly high increased risk of ten-year THA, which themselves reflect clinical thresholds used in practice.

Details of Data Handling

Deep Learning Segmentation

The study utilized 3 separate deep learning algorithms to measure 3 groups of radiographic features (joint space width, hip dysplasia angles, leg length discrepancy). Specifically, the study used a U-Net using a ResNet base architecture. This allowed for the leverage of a convolutional neural network (CNN) pre-trained on vast amounts of image data to conduct segmentation, requiring limited additional tuning with task-specific training data [44]. U-Nets were utilized to identify bony landmarks necessary to measure relevant radiographic measurements with ground truths established from manual segmentation. Performances of the U-Net models for landmark prediction were assessed using multi-class dice coefficients and foreground accuracies [45]. All baseline AP pelvis radiographs were first normalized (adaptive histogram equalization) to allow for contrast enhancement and better visualization of detail for manual segmentation [46]. Landmarks of interest were chosen based on anatomical landmarks utilized in literature to measure the hip parameters of interest.

An additional, fourth deep learning model was used to determine the presence of an implant on the contralateral side. These values were compared against the presence of an implant on the contralateral hip, obtaining 100% accuracy among observations with this variable available in the data (Table 5).

To measure joint space, all images were resized to 720× 720 pixels as inputs for the U-Net. The femoral head center was identified by taking six anatomical landmarks on the femoral head and finding the circle of best fit [47]. A line was drawn on every radian from the center of femoral head to the inferior point on the acetabular sourcil. The joint space was measured along this line and four measurements of joint space were derived (Table 5). Similar methods were used to measure both hip dysplasia angles and leg length discrepancy (LLD) measurements using various bone landmarks. Final outputs were all rescaled to original dimensions and converted to mm scalars available in the DICOM metadata to ensure measurements on properly scaled images.

The fastai deep learning library (V2.3.0) was utilized for training and ResNet-34 served as the base architecture. Model optimization for the loss function, learning rate, hyperparameters, were all conducted using the fastai library [48]. From the entire cohort, 500 images were randomly selected for training and validation. This sample size of 500 was based on prior, similar studies conducting machine learning segmentation on radiographic imaging pertaining to orthopedic treatment [47, 49]. The training and validation sets were randomly formed by splitting the 500 images in an 8:2 ratio (400 images training:100 images validation). Data augmentation was applied with rotation, zoom, wrap transformations. The multi-class dice coefficient as well as training and validation loss (Table 2) was utilized to monitor model performance over 75 epochs and the model with the highest multi-class dice coefficient was chosen as the final model. The models were trained on a NVIDIA Tesla K80 Graphics Processing Unit (GPU) with 12 gigabytes of RAM. Batch size was set to 2 or 4 for the models due to memory limitations. The final models were used to measure the available AP pelvis radiographs at the baseline visit.

GA2Ms Missing Data

GA2Ms allow for straightforward handling of missing values because of their nonparametric nature. Unlike logistic regression, missing continuous values for a particular variable can be imputed to arbitrary, invalid values of that variable, allowing the risk associated with a missing value to be viewed alongside the valid domain of that same variable on that variable's partial dependency plot. Two types of missing values were considered. If the underlying radiograph was entirely missing for a given hip, all radiographic variables for that hip were assigned the minimal value among non-missing values minus five. If the radiograph was not missing, but the resulting CNN-derived radiographic measurements were predicted to be outside clinically plausible ranges based prior literature [23], radiographic variables assigned either minimum value minus ten (if implausibly low) or the maximum value plus ten (if implausibly high).

Results

Characteristics of the Training and Validation Set

A total of 4,796 patients (9,592 hips) were included from the training data (mean age (SD), 61 (9); 5,608 (58%) female). Characteristics of each cohort are detailed in Table 4 below. Within the ten-year time frame, 230 (2.4%) hips underwent a THA. Mean time to THA among these 230 hips was 4.87 years (SD: 2.46, range: 0.19-9.01, IQR: 2.93-7.00).

TABLE 4

Characteristics of training and validation cohorts

| Characteristics* | Training Cohort** N = 7,672 hips, 3,836 patients | Validation Cohort** N = 1,920 hips, 960 patients |
|---|---|---|
| Demographics | | |
| Age, mean (SD) | 61 (9.2) | 61 (9.1) |
| BMI, mean (SD) | 28.6 (4.8) | 28.6 (5.0) |
| Female sex, N (%) | 4,466 (58) | 1,142 (59%) |
| Race | | |
| White | 6,042 (79%) | 1,538 (80%) |
| Black | 1410 (18%) | 338 (18%) |
| Asian | 70 (1%) | 20 (1%) |
| Other | 150 (2%) | 24 (1%) |
| Medical/Social History | | |
| Hip pain (ipsilateral), N (%) | 1,287 (17%) | 318 (17%) |
| Knee pain (ipsilateral), N (%) | 3,400 (44%) | 881 (46%) |
| Back pain, N (%) | 1,218 (16%) | 312 (16%) |
| Analgesic use, N (%) | 1,854 (24%) | 460 (24%) |
| Narcotic use, N (%) | 374 (5%) | 94 (5%) |
| Charlson score, mean (SD) | 0.3 (1.05) | 0.4 (1.03) |
| History of arthritis, N (%) | 338 (4%) | 68 (4%) |
| History of Heberden's nodes, N (%) | 2,334 (30%) | 664 (35%) |

TABLE 4-continued

Characteristics of training and validation cohorts

| Characteristics* | Training Cohort** N = 7,672 hips, 3,836 patients | Validation Cohort** N = 1,920 hips, 960 patients |
|---|---|---|
| History of diabetes, N (%) | 576 (8%) | 148 (8%) |
| History of heart attack, N (%) | 192 (3%) | 44 (2%) |
| Former or Current Smoker, N (%) | 1,426 (19%) | 368 (20%) |
| SF-12 (mental), mean (SD) | 52.9 (9.9) | 53.1 (9.3) |
| CES-Depression, mean (SD) | 6.45 (7.1) | 6.45 (7.0) |
| Surgical History | | |
| Previous hip surgery (contralateral), N (%) | 75 (1%) | 18 (1%) |
| Previous knee surgery, N (%) | 991 (13%) | 251 (13%) |
| Previous knee scope, N (%) | 757 (10%) | 200 (10%) |
| Family History | | |
| Hip replacement, N (%) | 672 (9%) | 186 (10%) |
| Knee replacement, N (%) | 1,034 (13%) | 292 (15%) |
| Knee and Hip Assessment | | |
| WOMAC, mean (SD) | 12.0 (15.4) | 11.7 (14.9) |
| KOOS (pain), mean (SD) | 84.5 (18.0) | 84.5 (17.5) |

*Abbreviated list of demographic and clinical variables. Full list is available in Table 1.
**Randomization required both hips from the same patient were in the same training or validation cohort to prevent data leakage U-Net Segmentation Performance of Bone Landmarks and Measurements Segmentation results are described in Table 5 below. All three models, which measured joint space width, dysplasia angles, and leg length discrepancy, respectively, had multi-dice coefficients >0.88 and foreground accuracies >0.92, indicating good segmentation performance [7]. Joint space widths were measured at a rate per 10.36 s per image, dysplasia angles at 2.32 s per image, and LLD at 1.13 s per image.

TABLE 5

Deep learning segmentation results

| Model* | Landmarks** | Multi-Dice Coefficient | Foreground Accuracy |
|---|---|---|---|
| Joint Space Width | Femoral Head Acetabular Sourcil | 0.93 | 0.97 |
| Dysplasia Angles | Femoral Head Acetabular Sourcil Pelvis Teardrop Obturator Foramen | 0.89 | 0.96 |
| Leg Length Discrepancy | Femoral Head Pelvis Teardrop Obturator Foramen Femoral Trochanters Ischial Tuberosity | 0.88 | 0.92 |

Figure 8A:
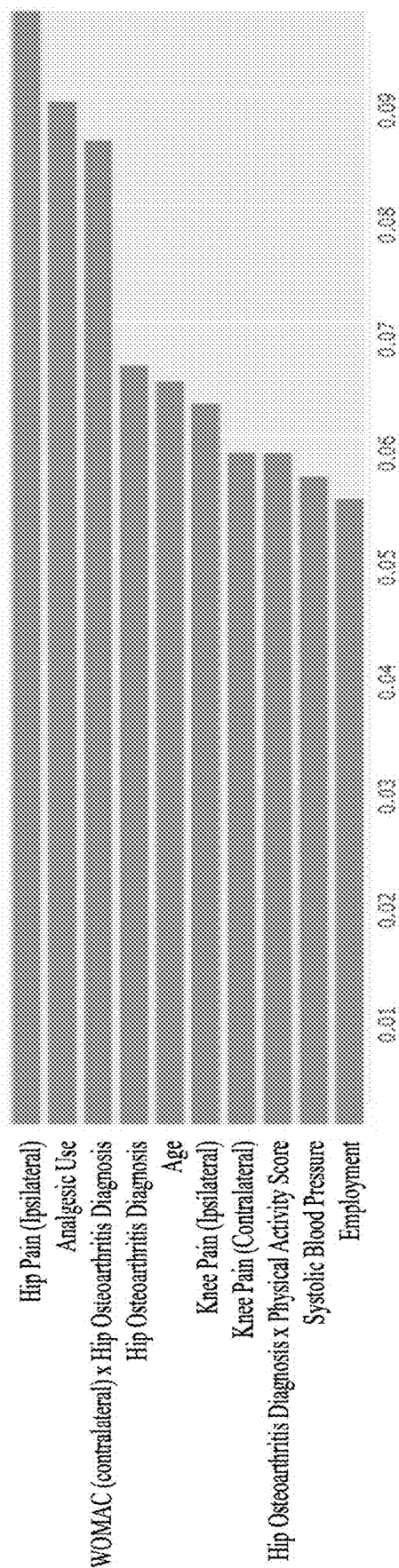
FIG. 8A is a bar graph for the baseline (demographic and clinical) GA2M ML model identifying the top demographic features.
Figure 8B:
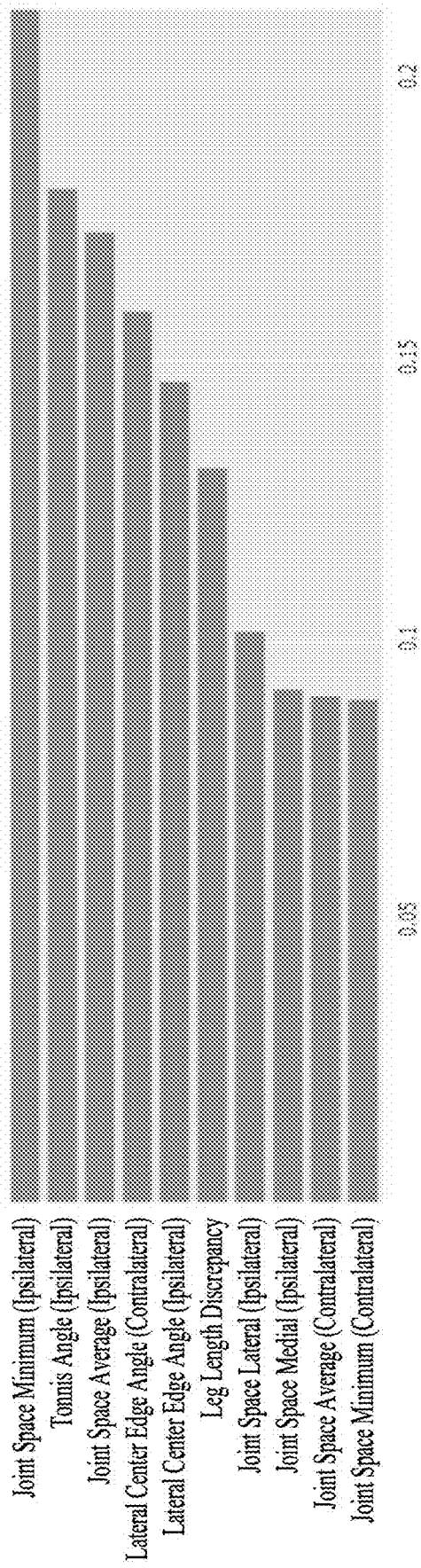
FIG. 8B is a bar graph for the radiographic (radiographic measurements) GA2M ML model identifying the top radiographic features.
Figure 8C:
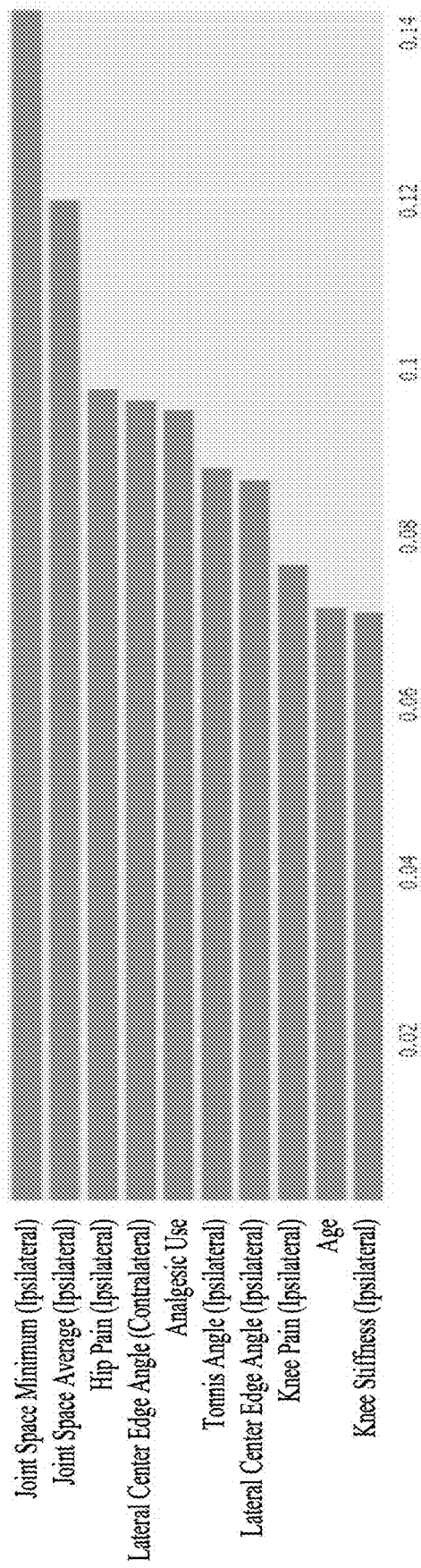
FIG. 8C is a bar graph for the combined radiographic and demographic GA2M ML model identifying the top radiographic and demographic features.
Figure 9A:
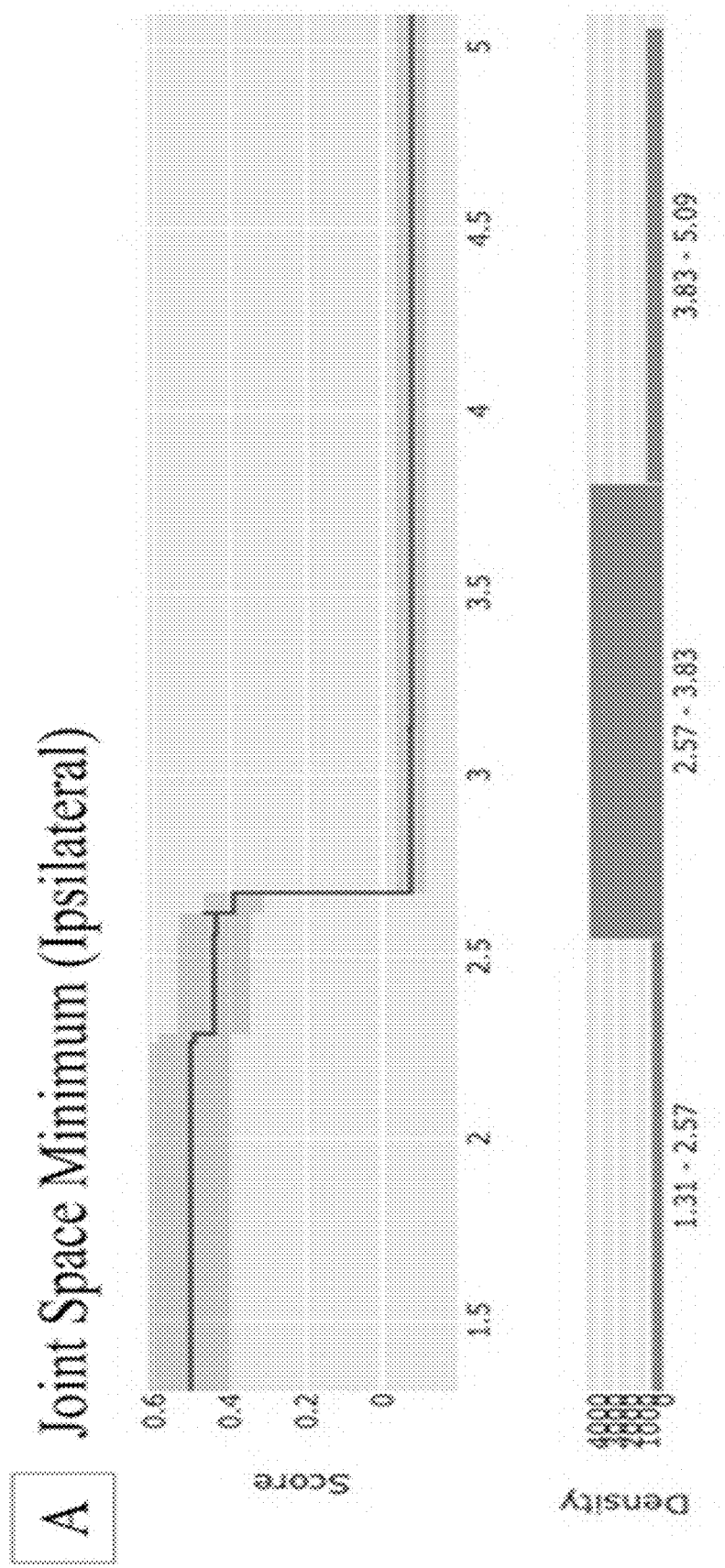
FIGS. 9A-9J are a collection of partial dependency plots for top predictive features of the combined radiographic and demographic model. The Score in the y-axis is the log odds for each feature at a given value. These scores are summed across features by the GA2M to predict the likelihood of the outcome of THA.
Figure 9B:
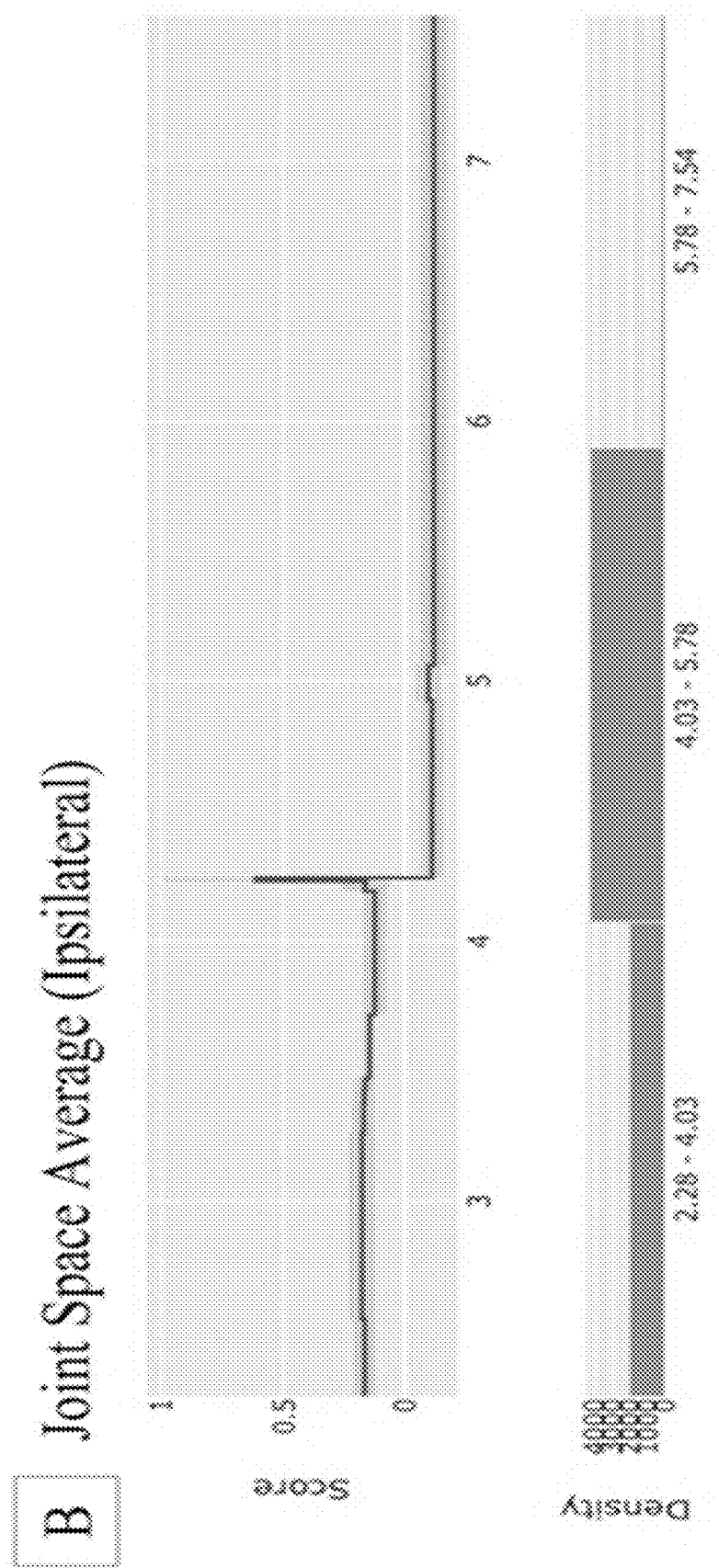
Figure 9C:
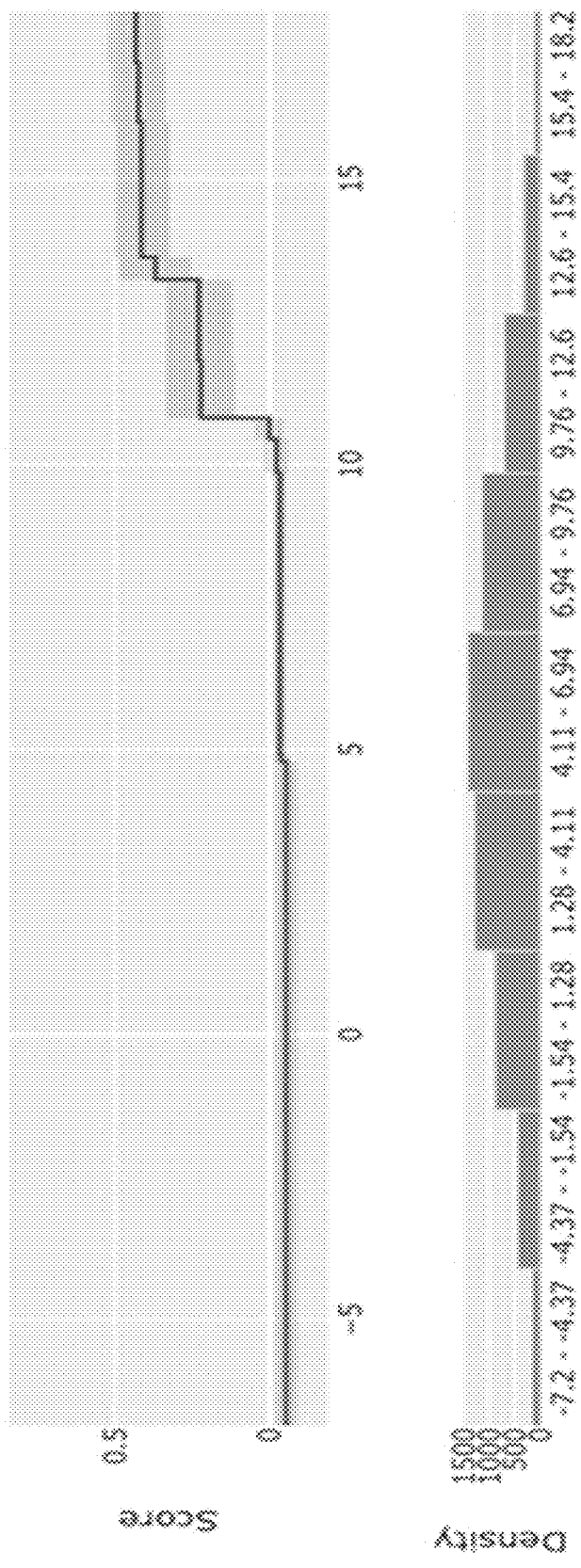
Figure 9D:
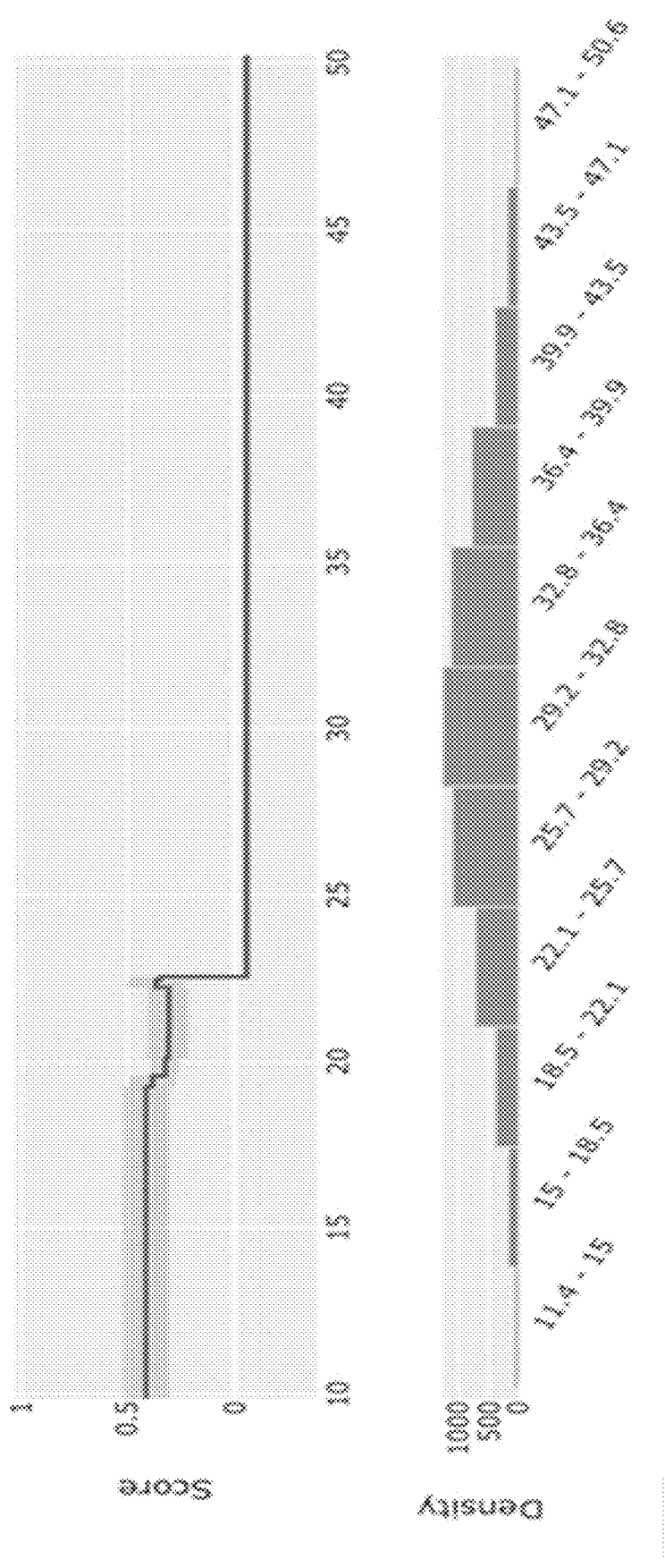
Figure 9E:
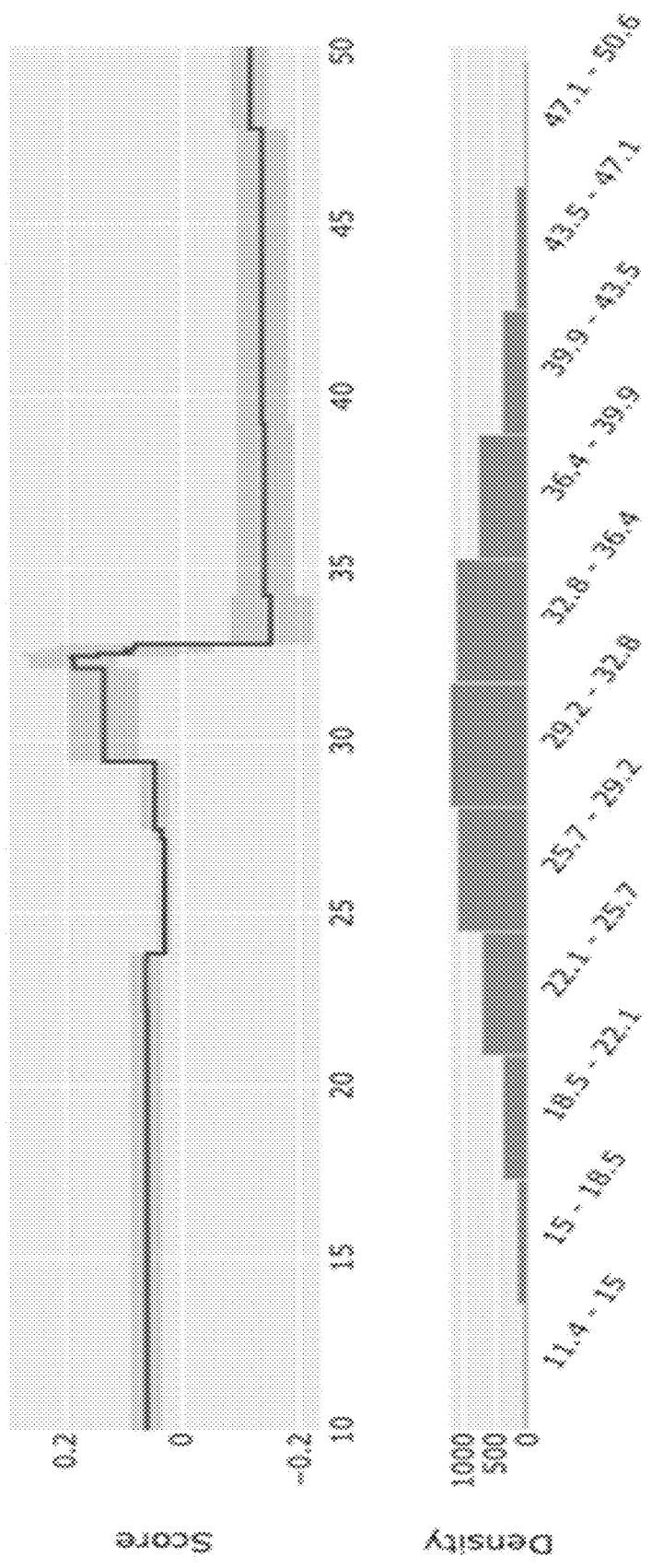
Figure 9F:
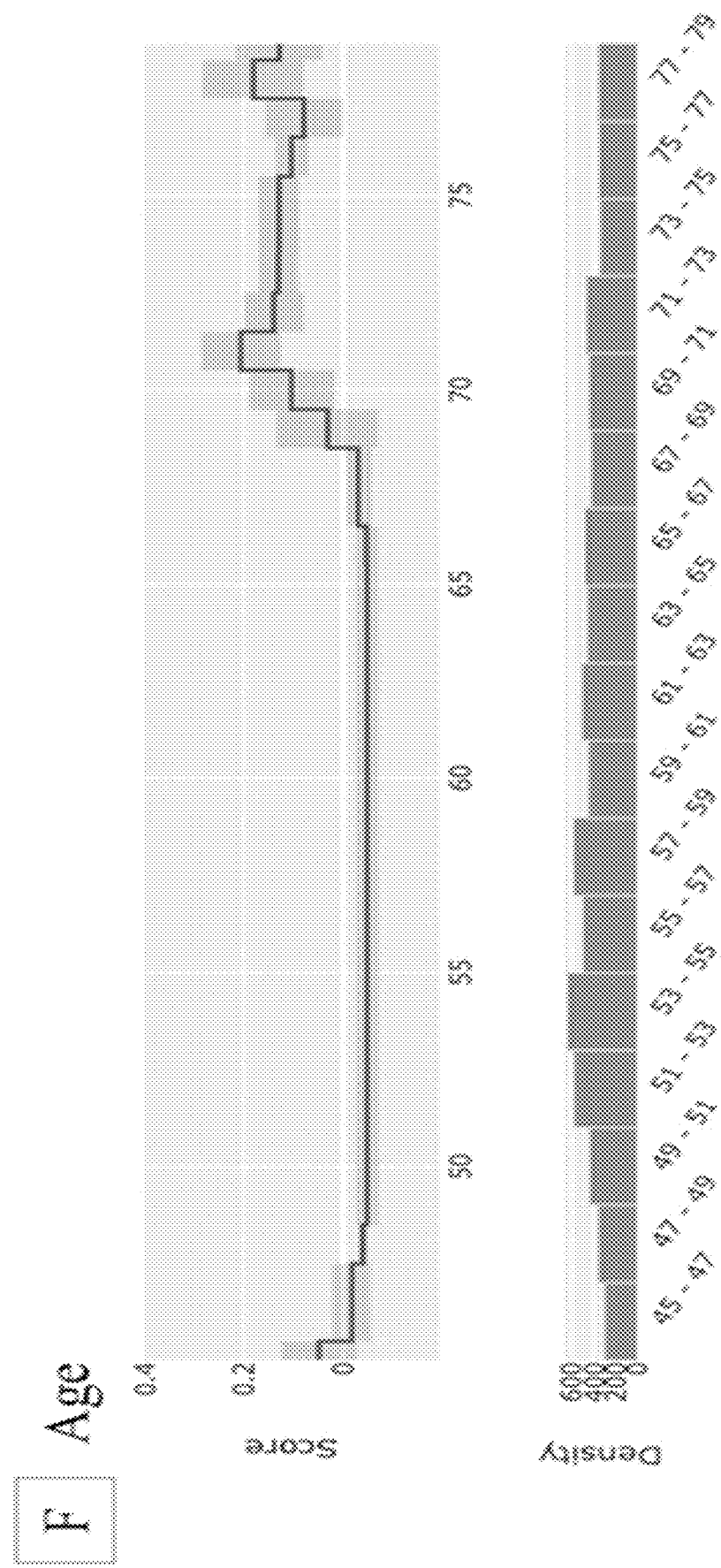
Figure 9G:
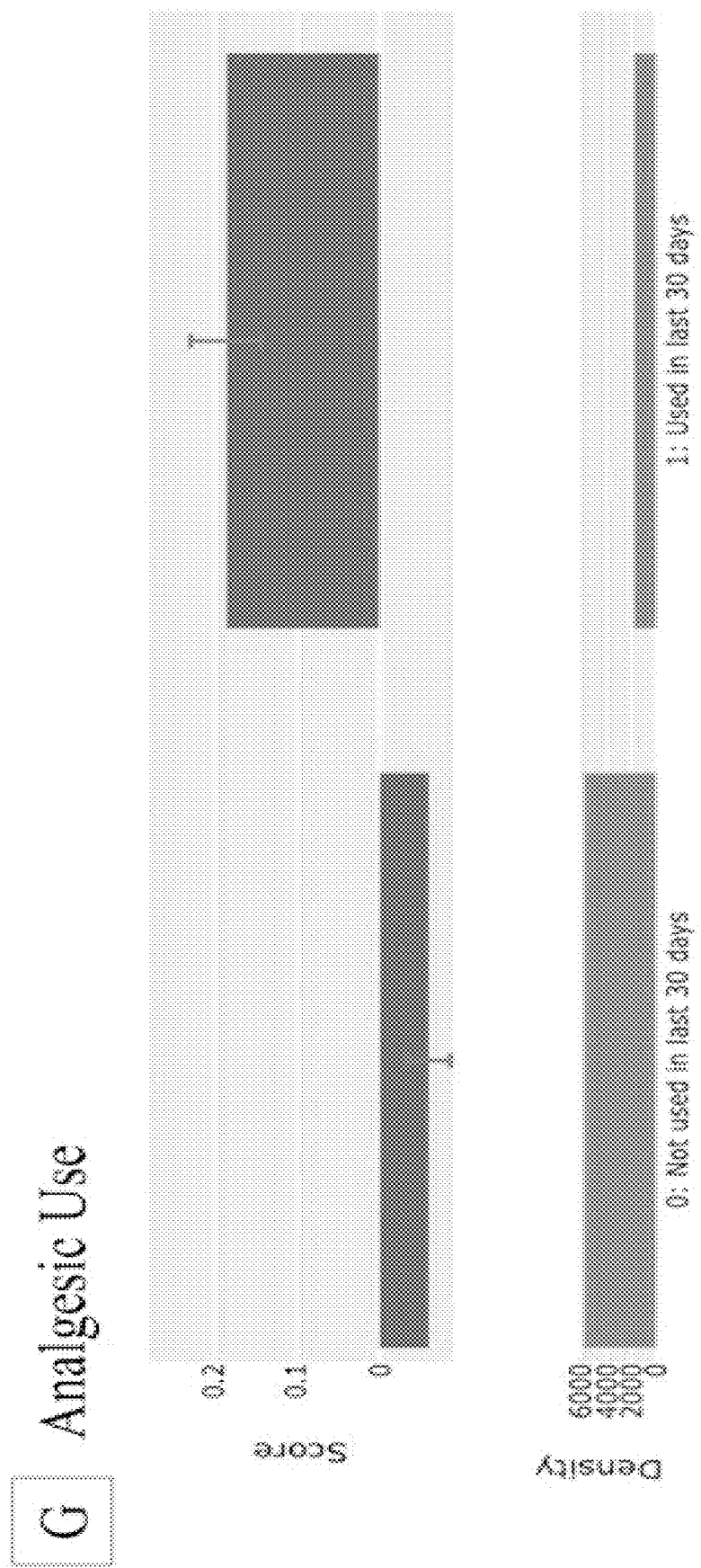
Figure 9H:
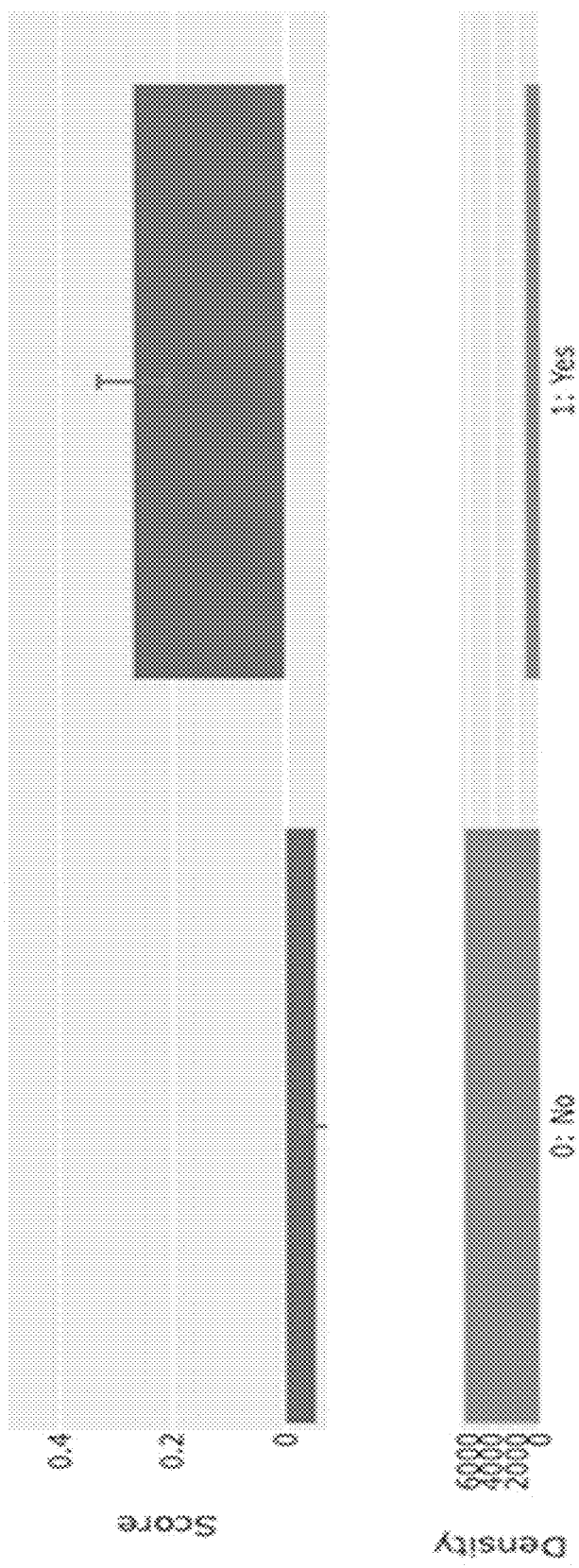
Figure 9I:
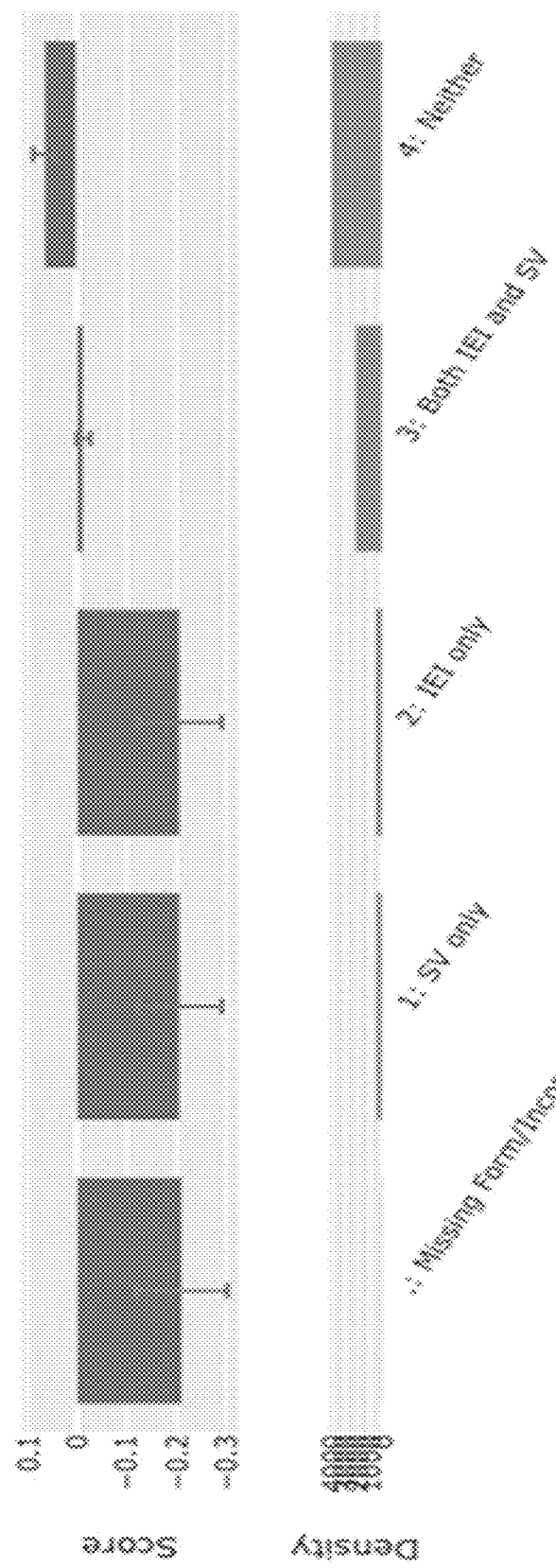
Figure 9J:
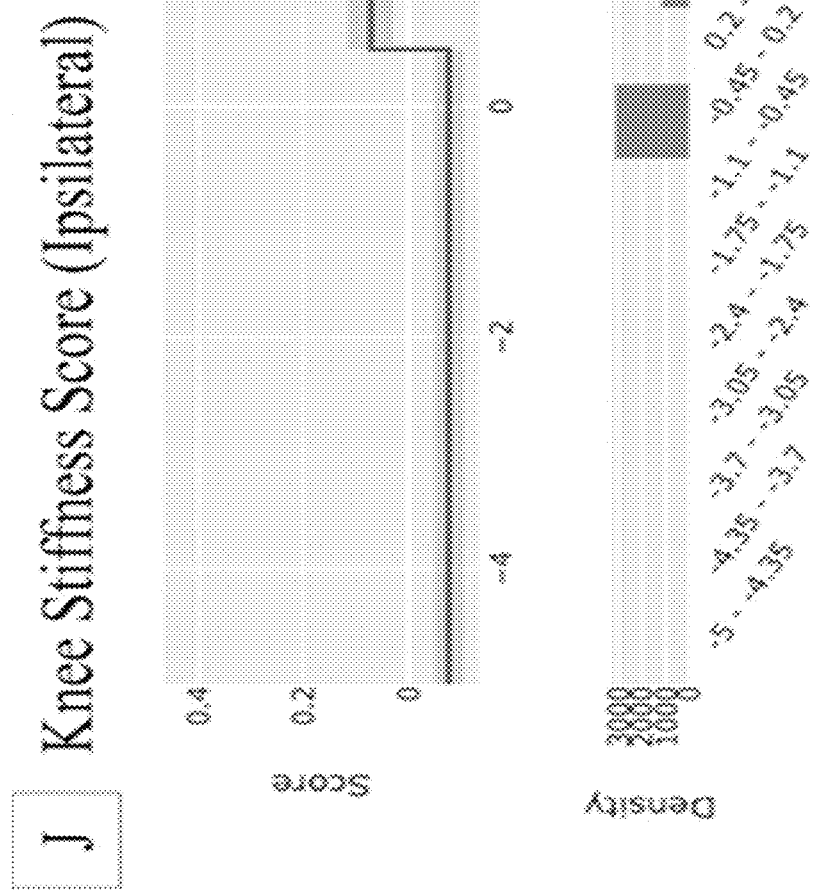
Figure 10A:
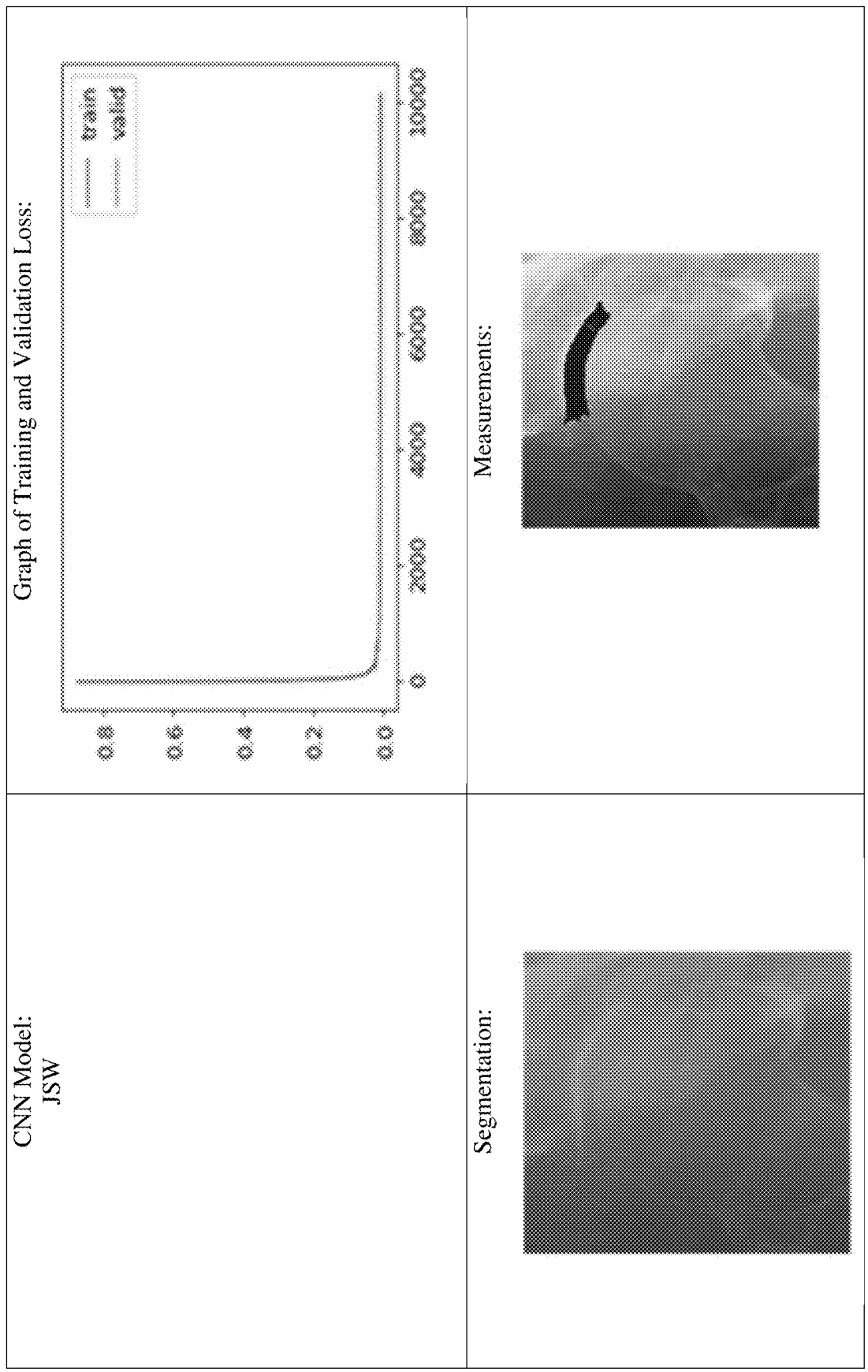
FIG. 10A is a table including the JSW SML model training and validation loss and segmentation outputs; and the PML model measurement outputs for JSW.
Figure 10B:
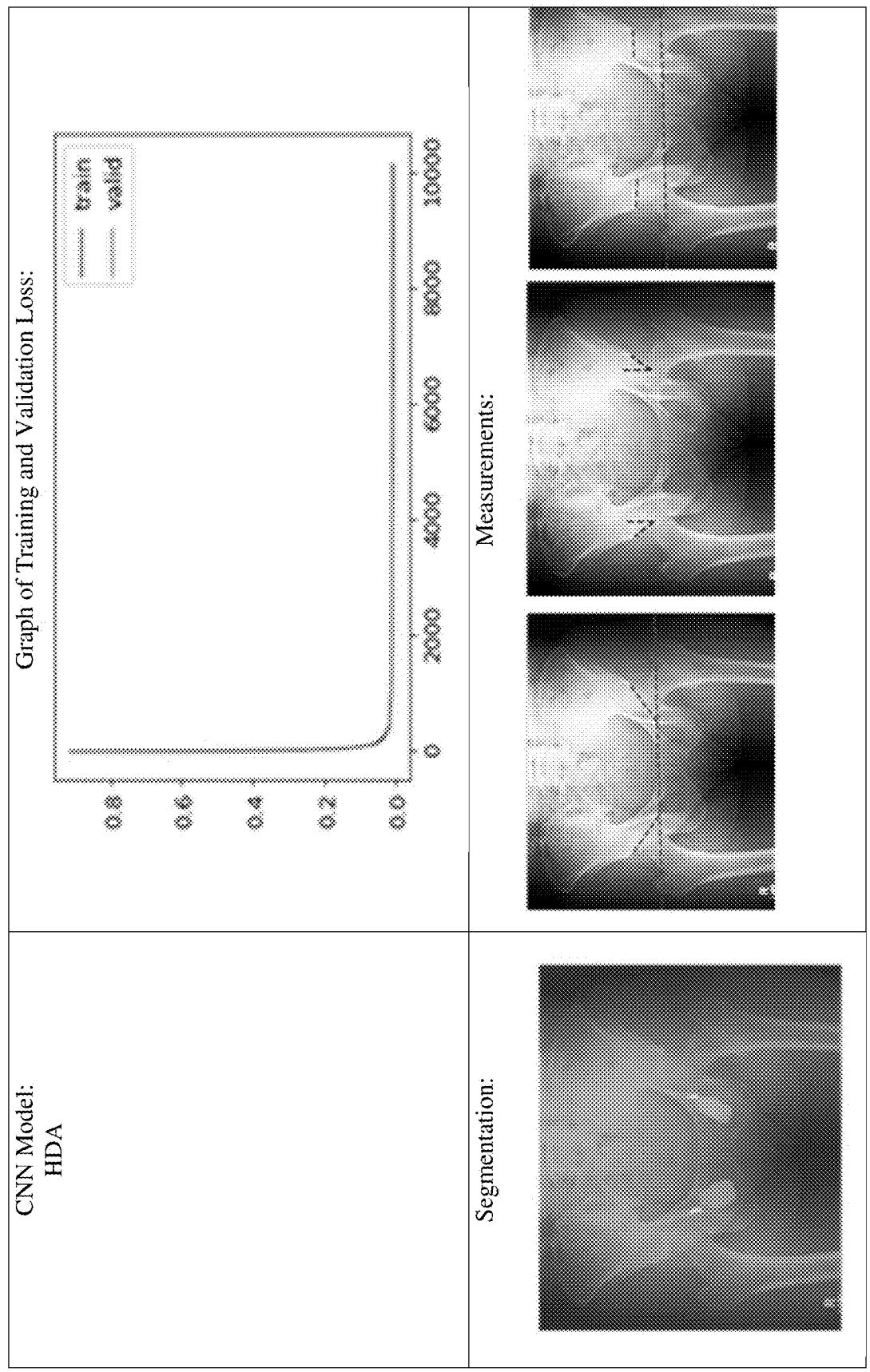
FIG. 10B is a table including the HDA SML model training and validation loss and segmentation outputs; and the PML model measurement outputs for HDA.
Figure 10C:
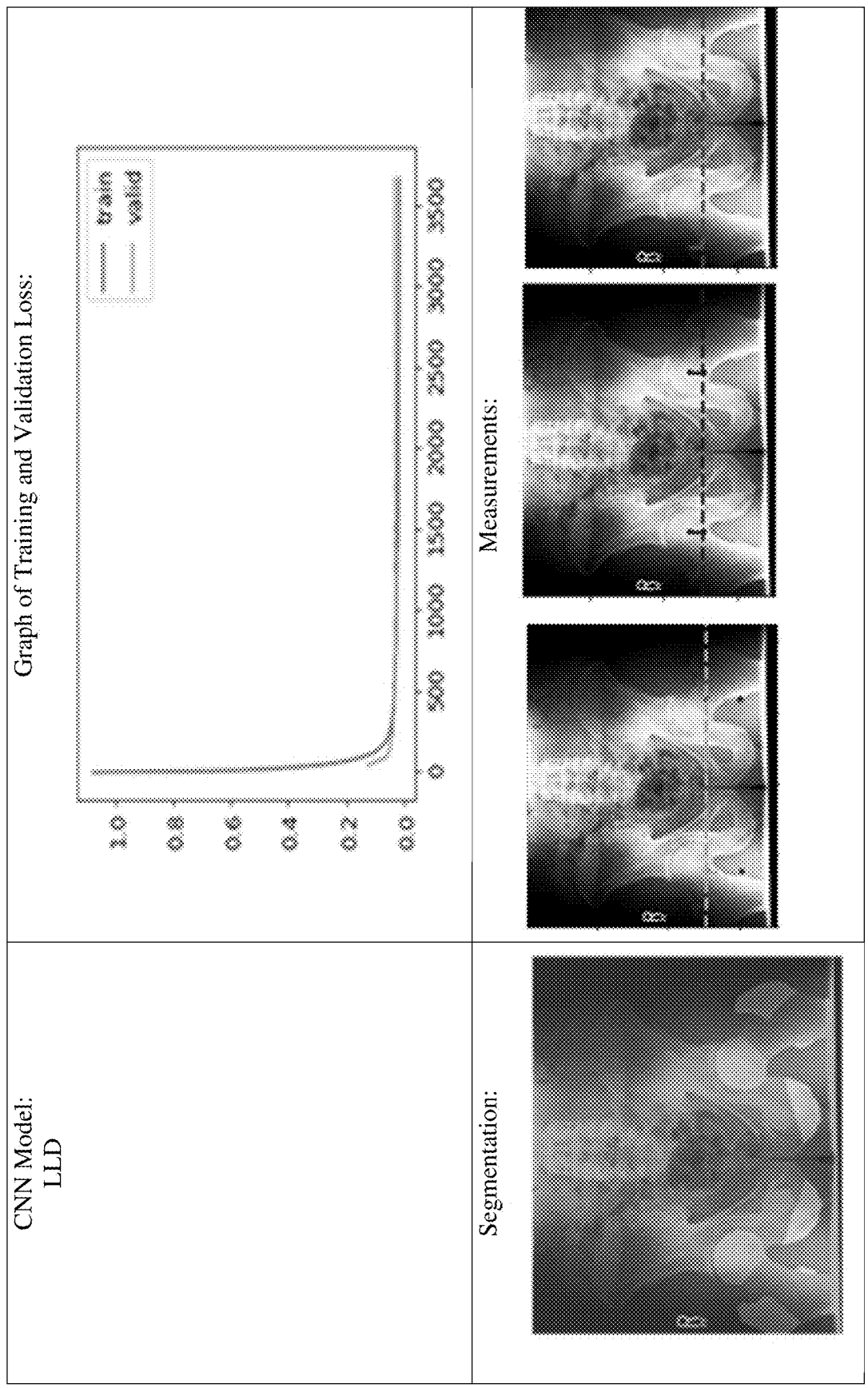
FIG. 10C is a table including the LLD SML model training and validation loss and segmentation outputs; and the PML model measurement outputs for LLD.
Figure 11A:
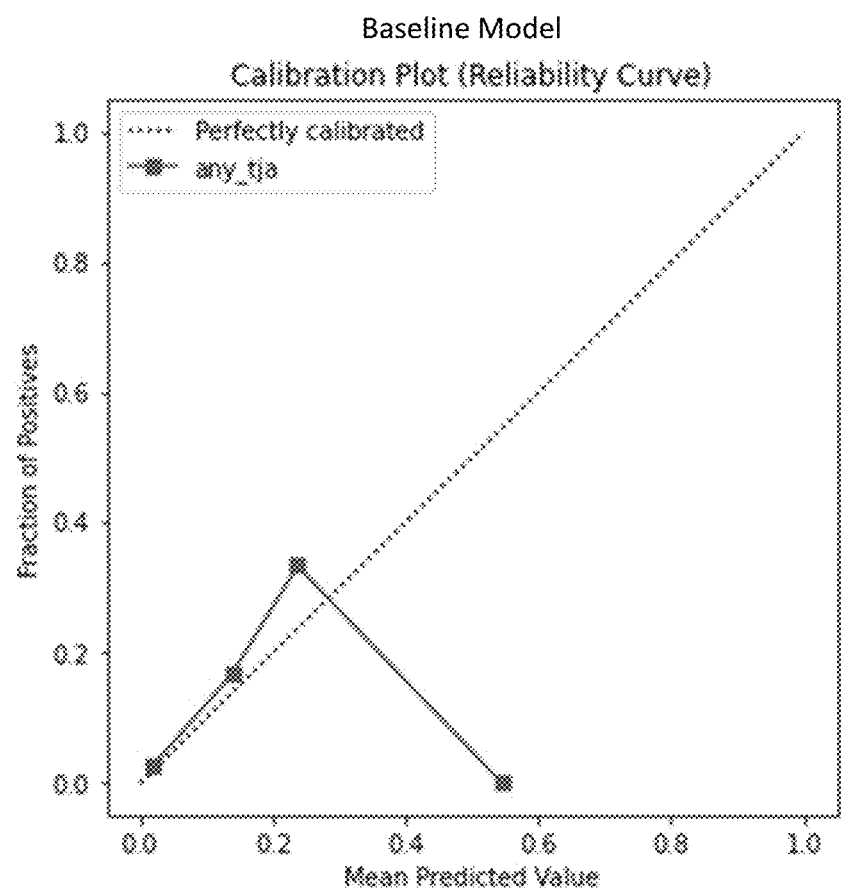
FIGS. 11A-11E are graphs of the full performance analysis for the baseline model.
Figure 11B:
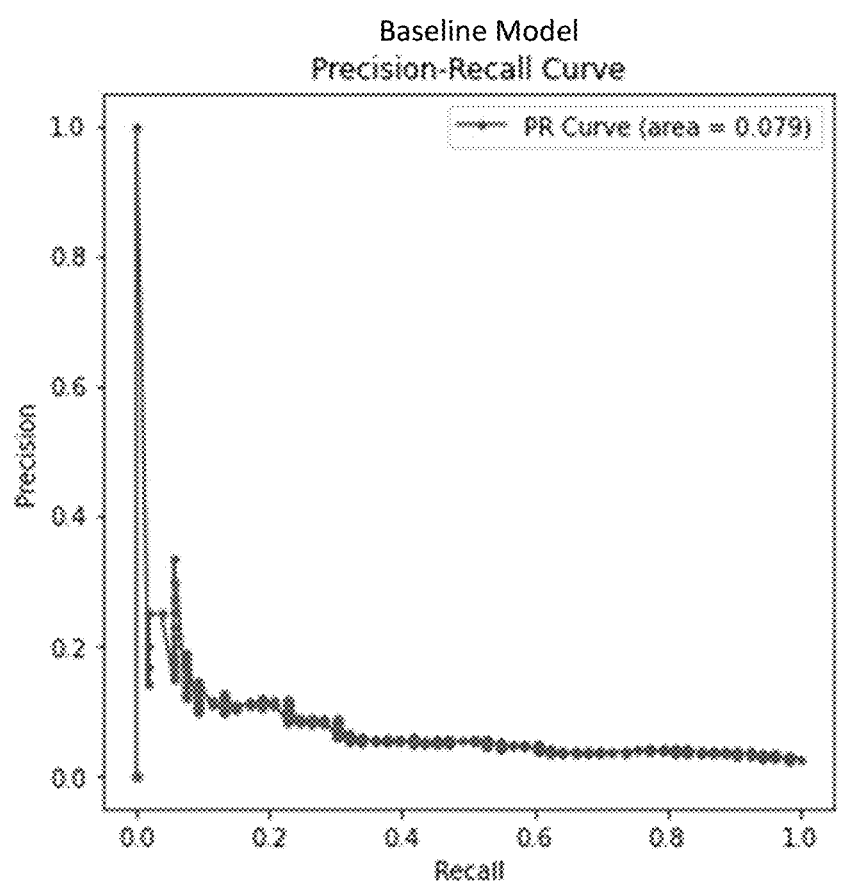
Figure 11C:
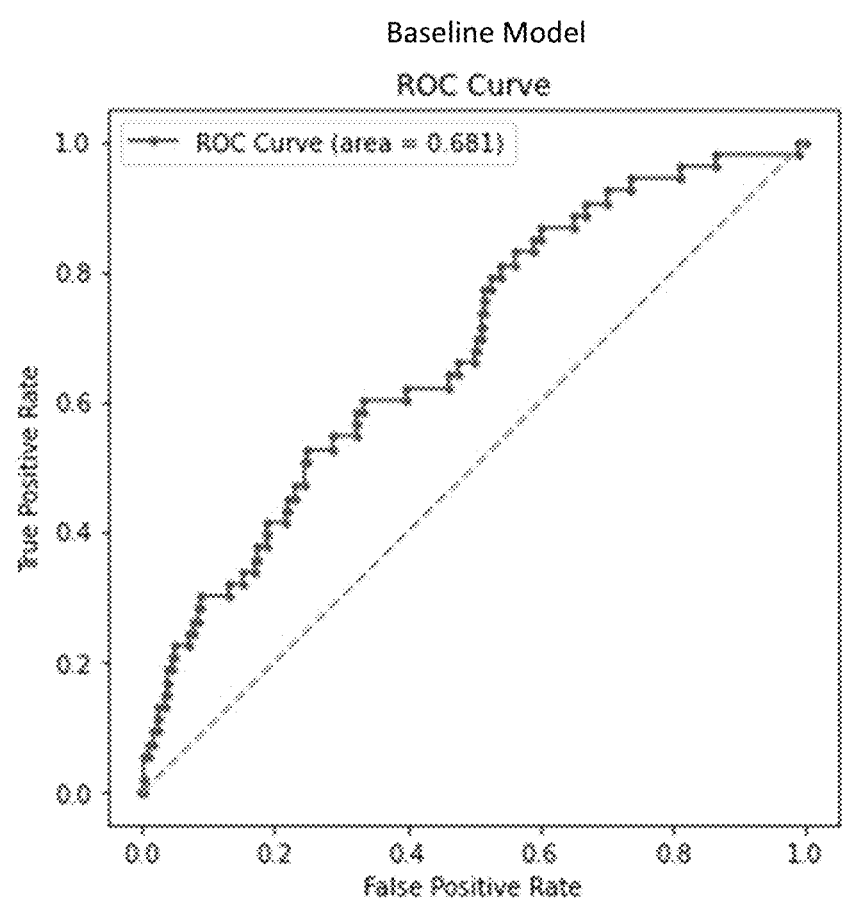
Figure 11D:
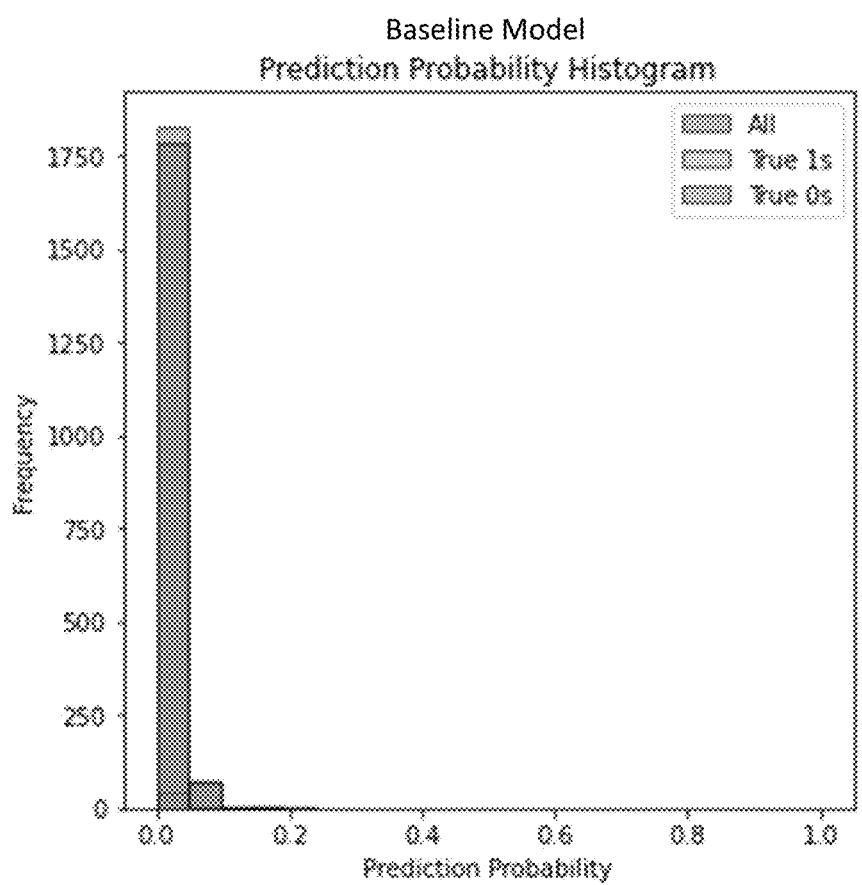
Figure 11E:
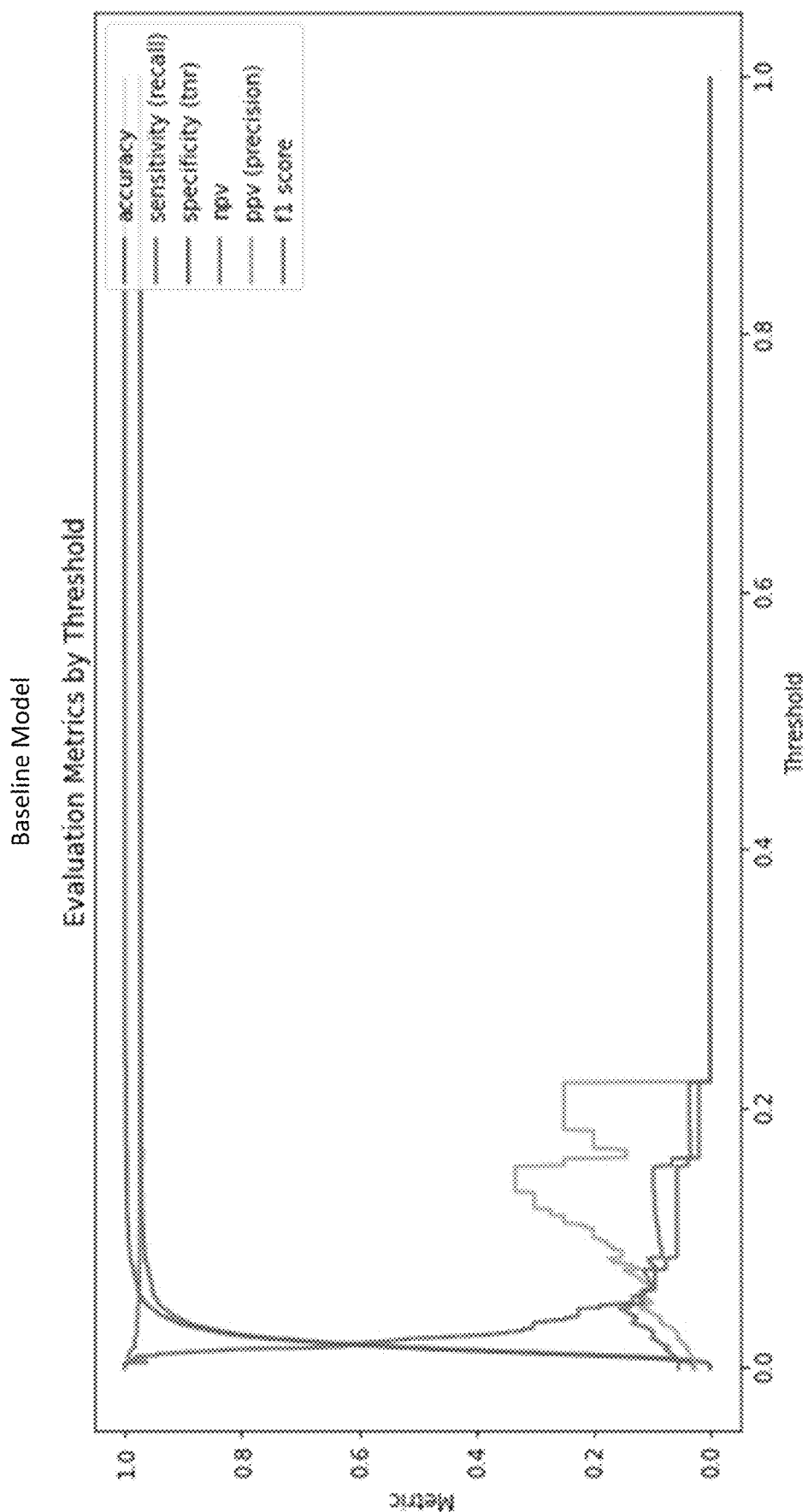
Figure 11F:
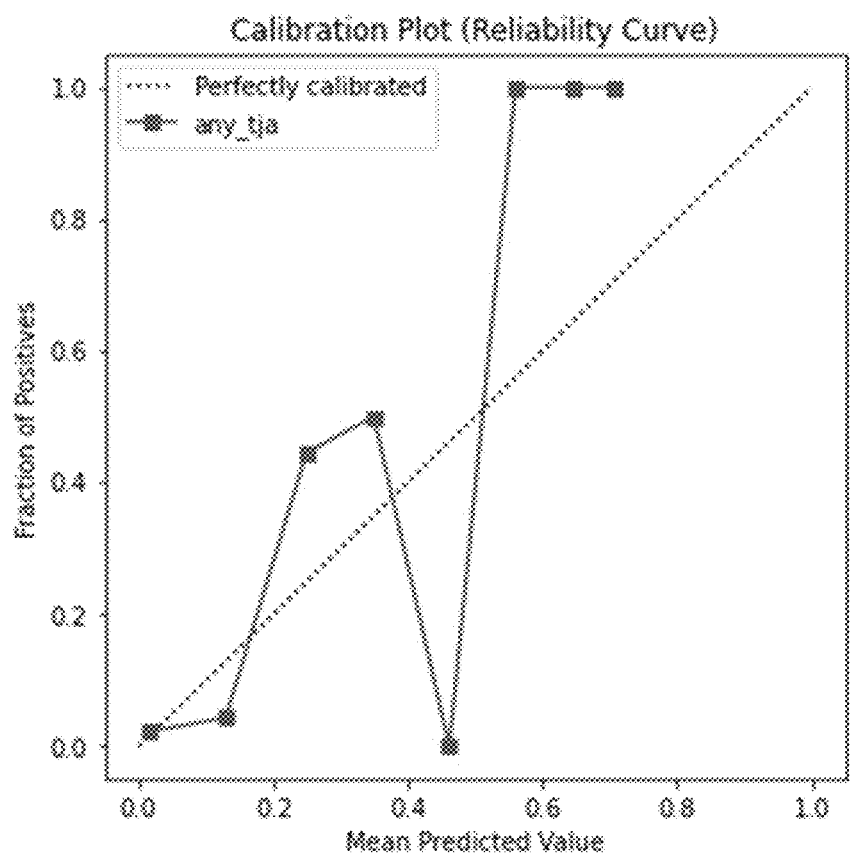
FIGS. 11F-11J are graphs of the full performance analysis for the radiographic model.
Figure 11G:
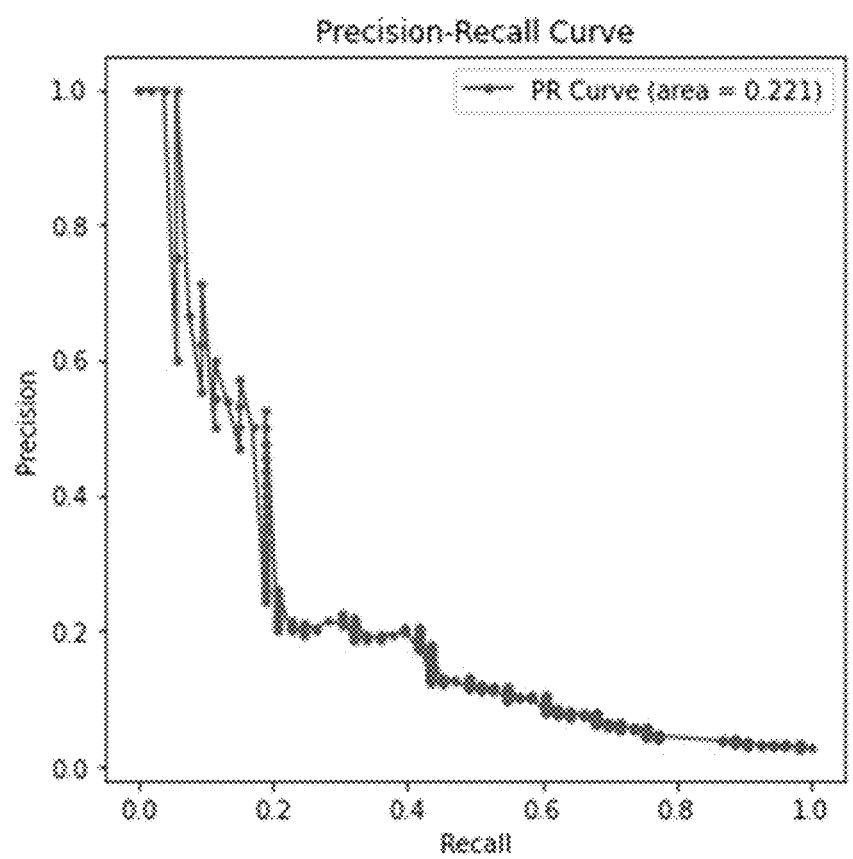
Figure 11H:
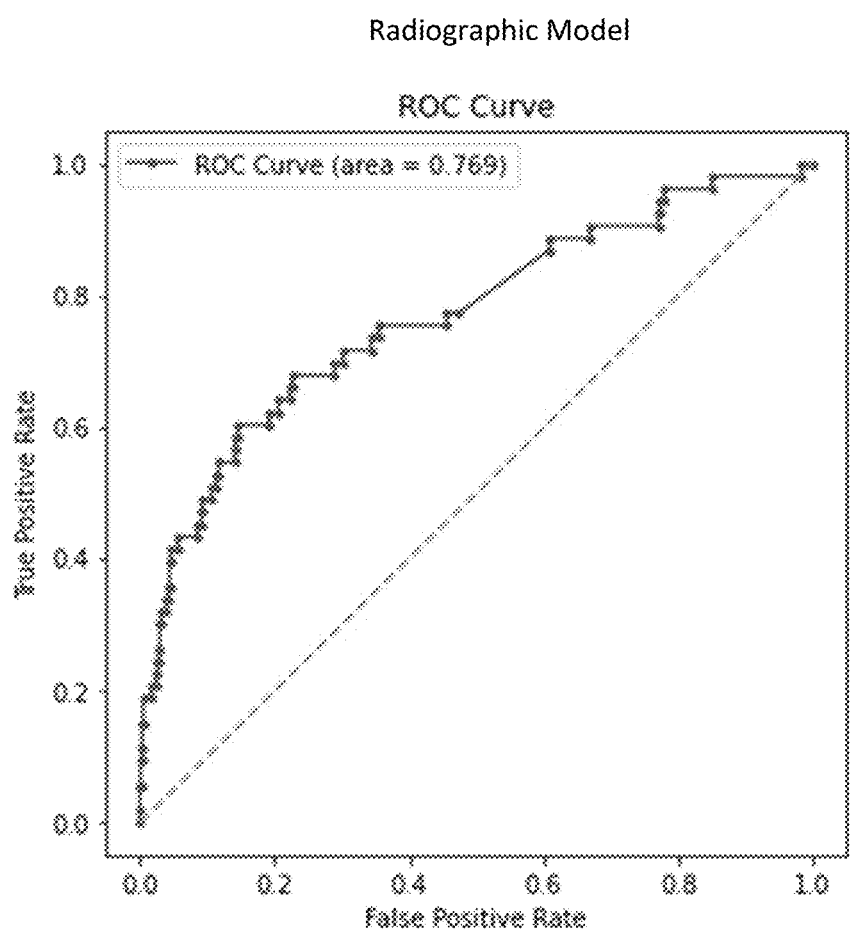
Figure 11I:
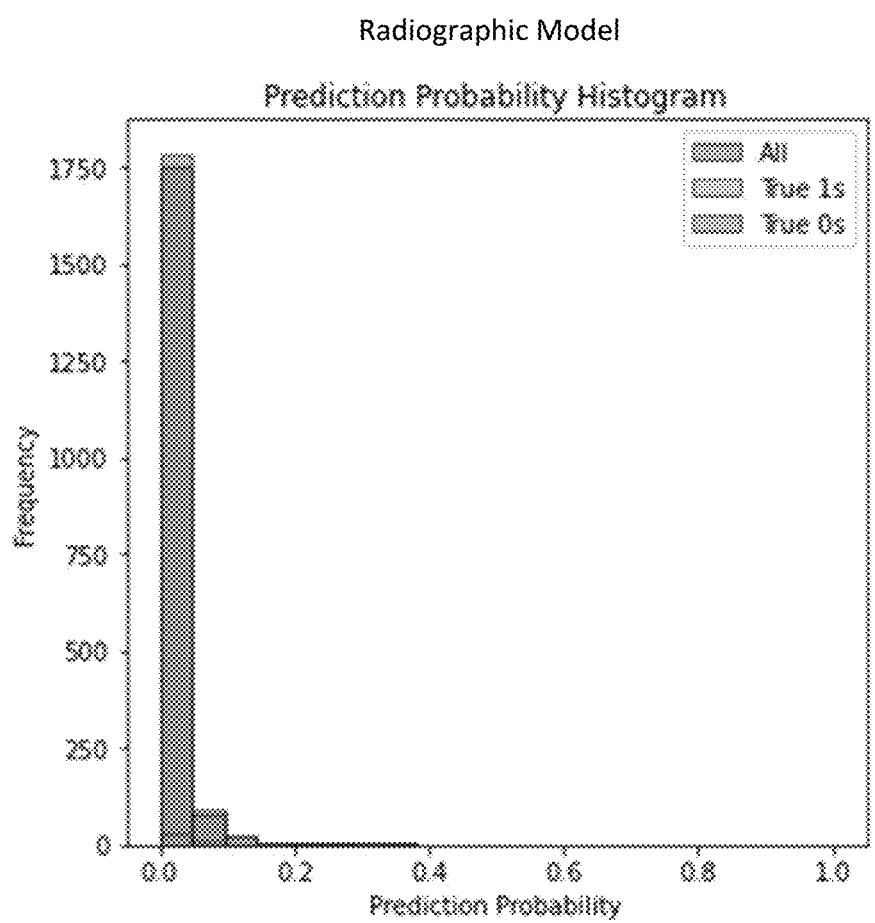
Figure 11J:
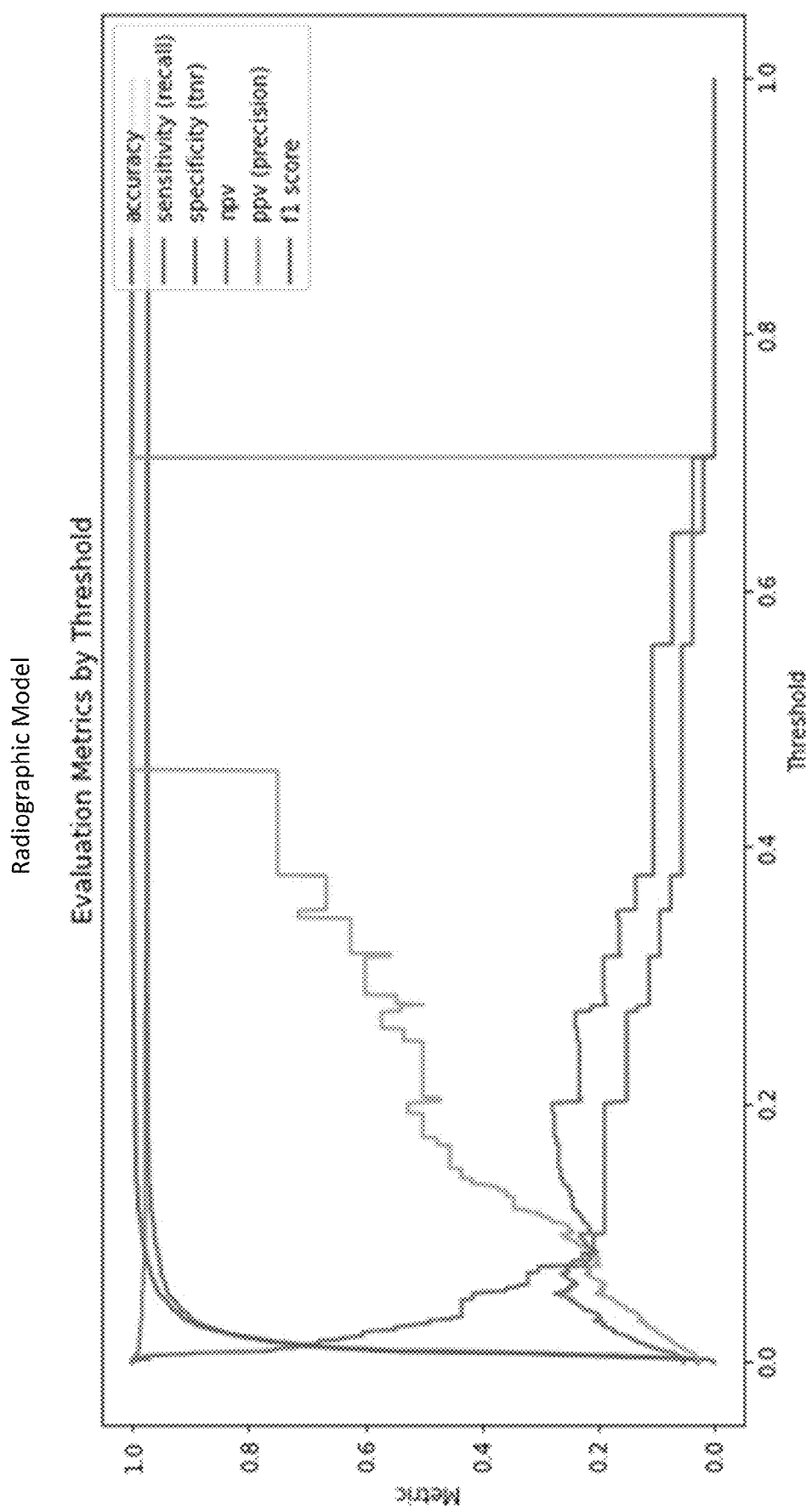
Figure 11K:
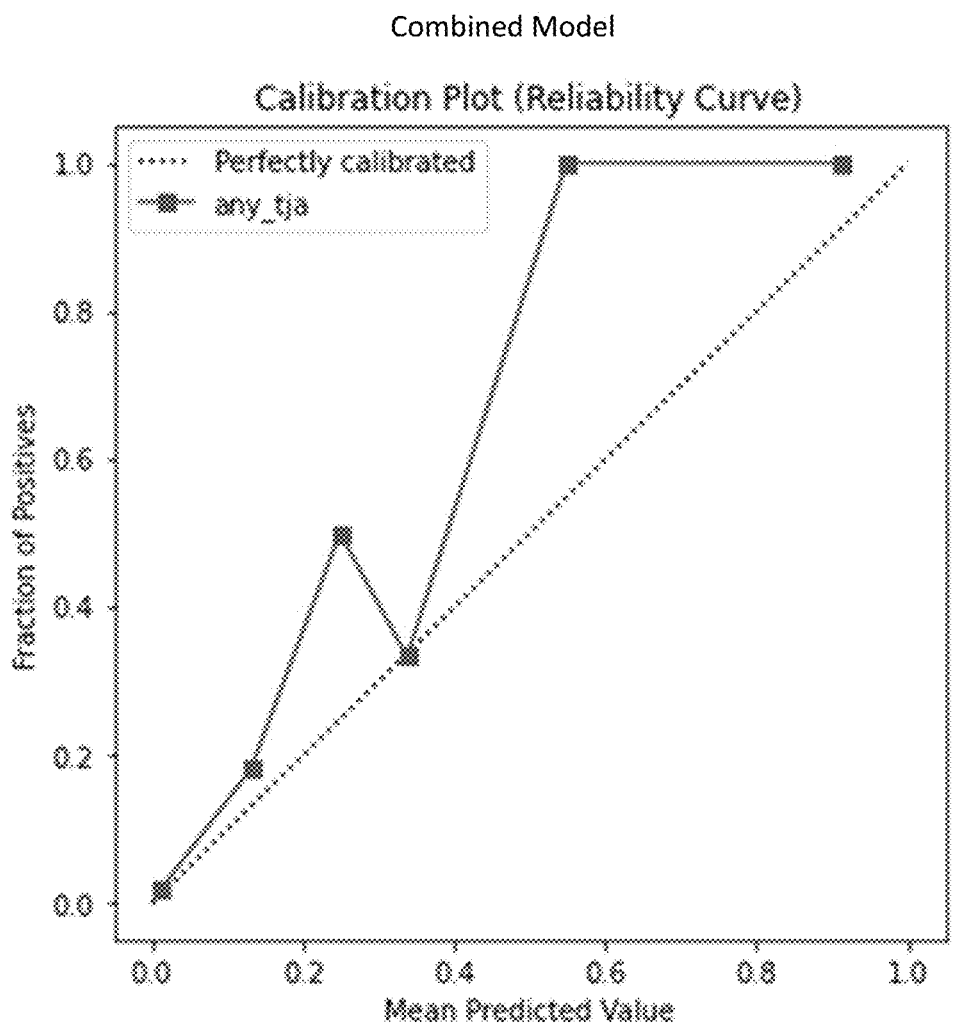
FIGS. 11K-11O are graphs of the full performance analysis for the combined model.
Figure 11L:
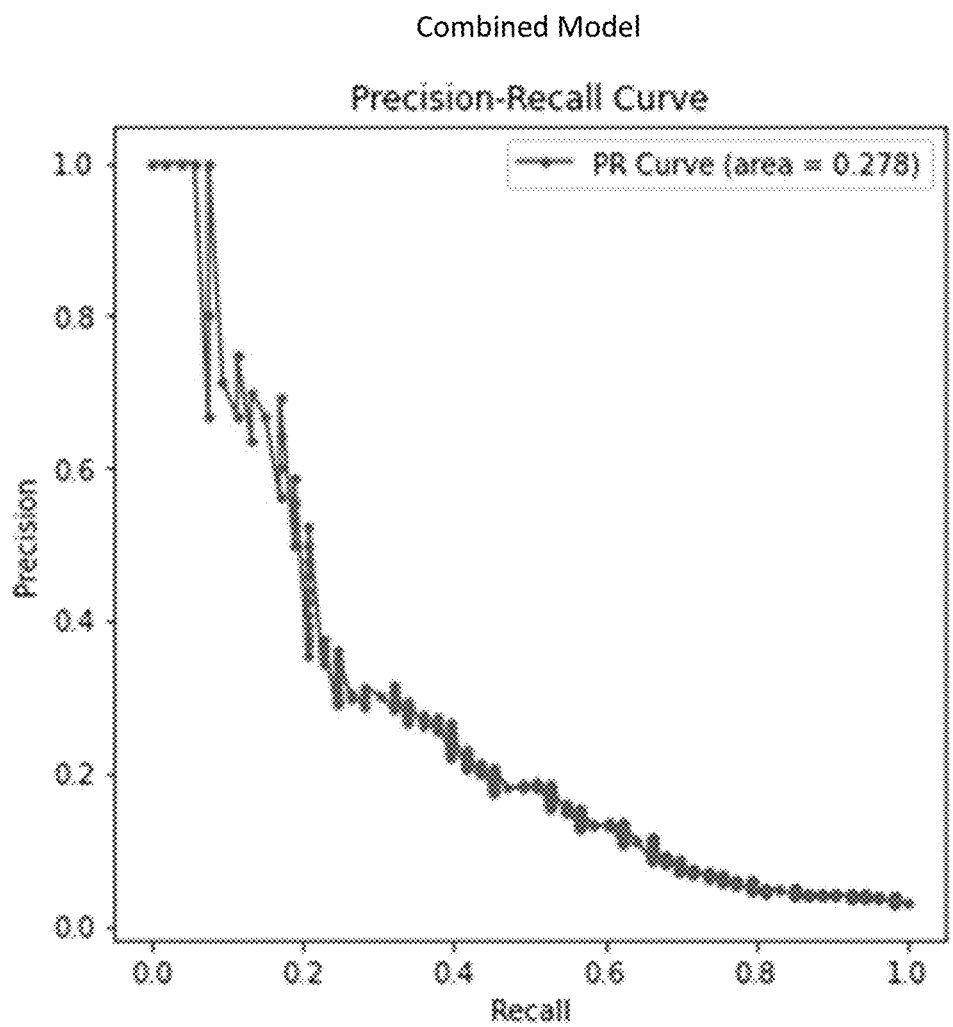
Figure 11M:
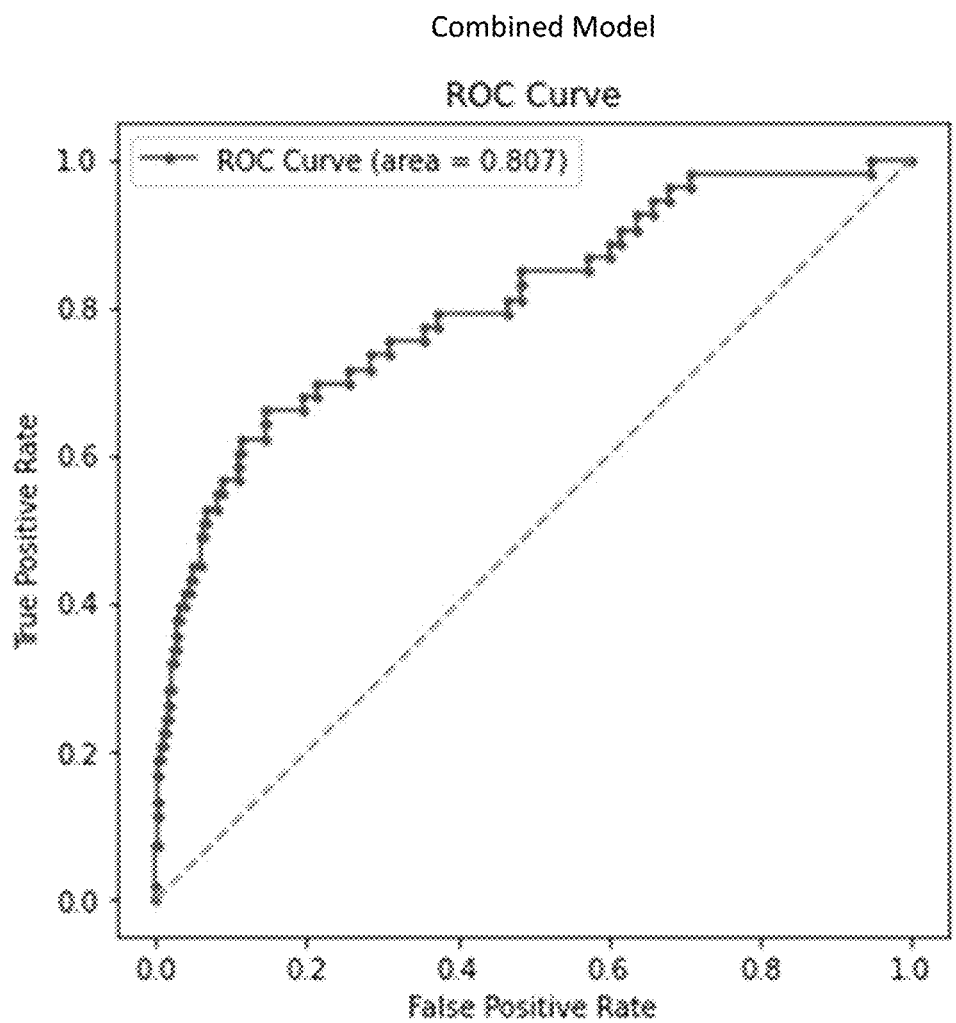
Figure 11N:
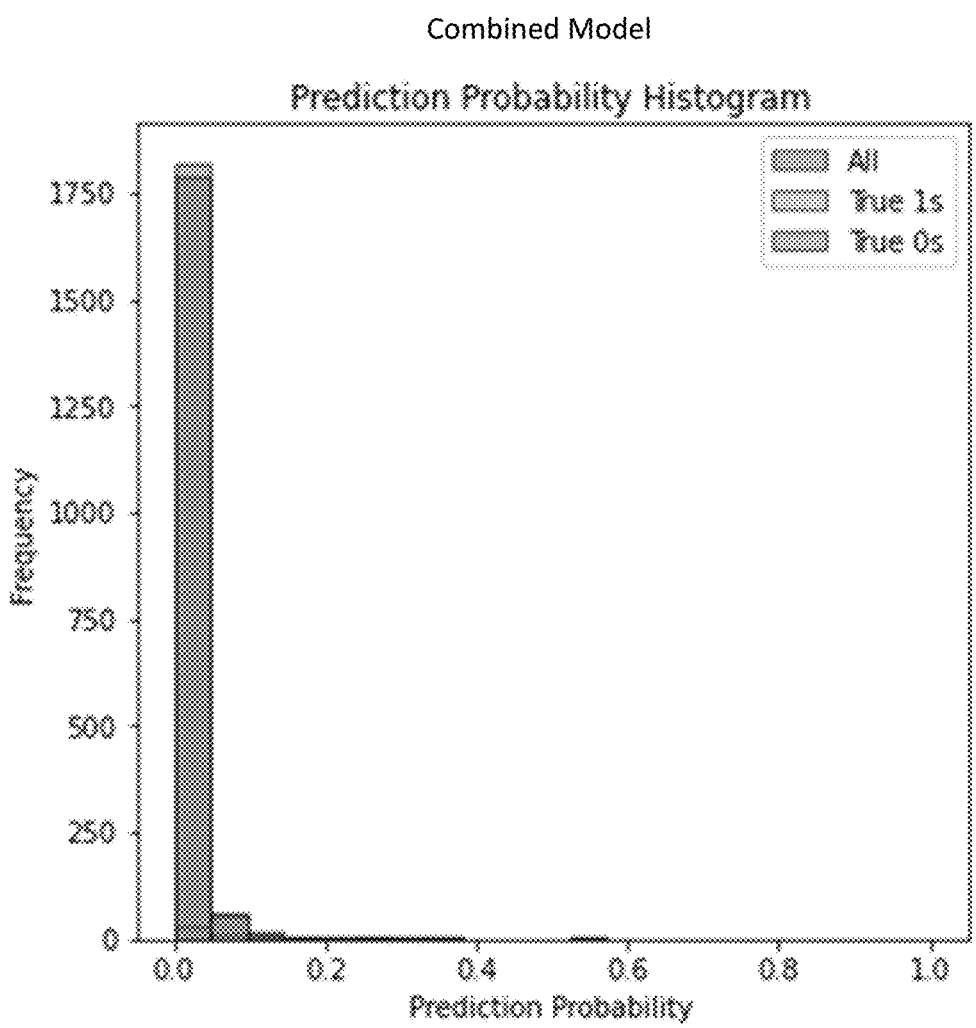
Figure 11O:
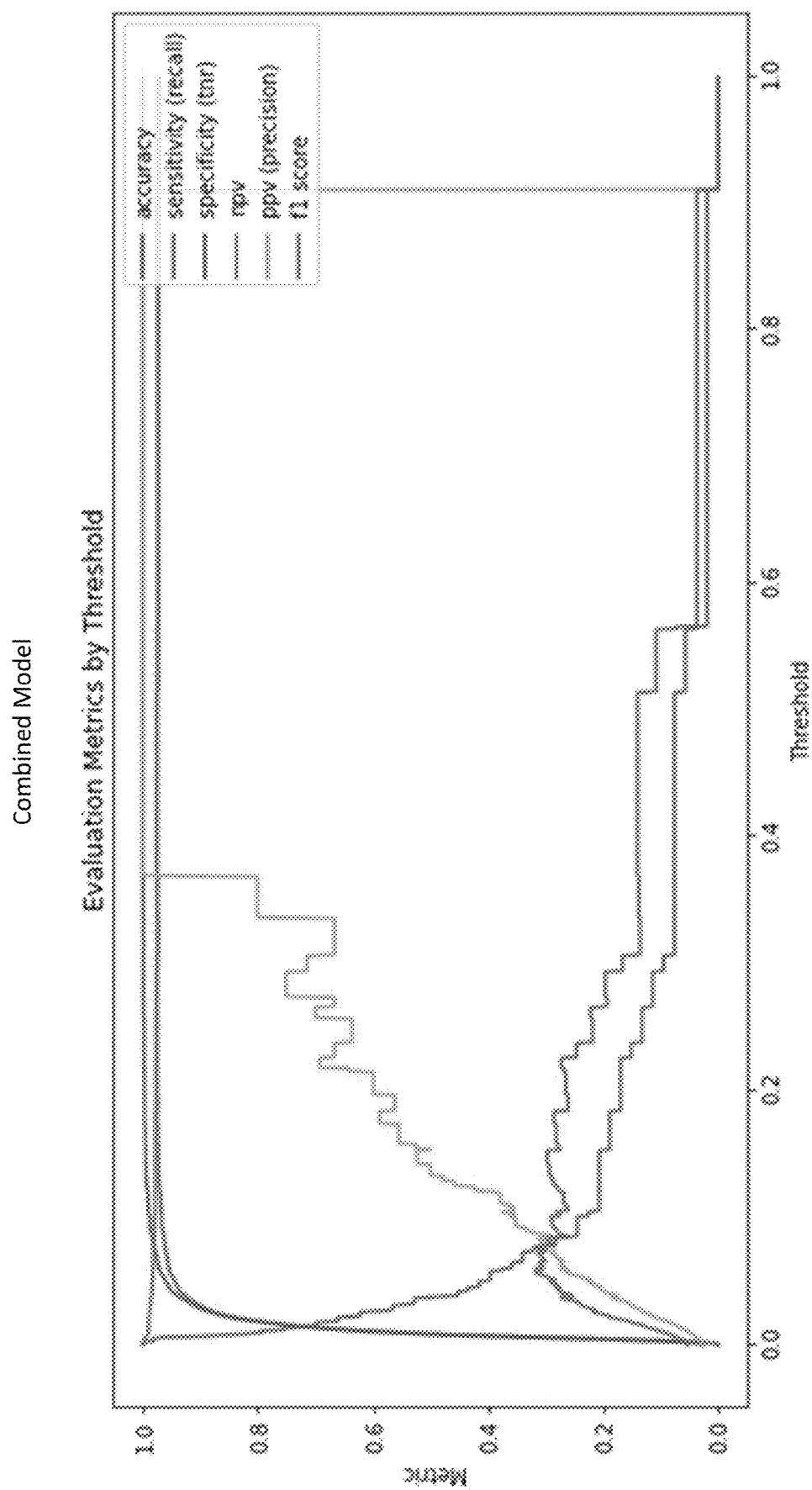

*Segmentation and measurement result available in FIGS. 10.
**Acetabular sourcil = sclerotic "eyebrow" on top of acetabulum (hip bone socket).
Teardrop = radiographic inferomedial bony confluence along acetabulum.
Obturator foramen = opening between the pelvic ischium and pubis.
Femoral trochanters = femur projections important for muscle attachments.
Ischial tuberosity = inferior projection of the ischium Baseline Model Performance Predicting THA The baseline model utilizing only demographic and clinical variables as features had an AUROC of 0.68 and an AUPRC of 0.085 (Table 6 below) for predicting ten-year THA on the testing cohort. Top features involved patient reported hip pain, analgesics use, previous hip OA diagnosis, age, and an interaction between hip pain and the contralateral side WOMAC disability score (FIG. 8).

TABLE 6

Baseline, radiographic and combined model performance

| Model performance metrics* | Baseline model (demographic and clinical) | Radiographic model (deep-learning measurements) | Combined model (all variables) |
|---|---|---|---|
| AUROC | 0.681 (0.609-0.752) | 0.769 (0.693-0.845) | 0.807 (0.741-0.874) |
| AUPRC | 0.079 (0.067-0.080) | 0.221 (0.167-0.226) | 0.279 (0.219-0.283) |

*See FIGS. 11 for calibration, accuracy, sensitivity, specificity, positive predictive value, negative predictive value, and F1 scores for each model.
AUROC = area under the receiver operating characteristic.
AUPRC = area under the precision-recall curve.
Numbers in parentheses indicate 95% confidence intervals derived from bootstrapping with 1000 iterations from the validation cohort.

Deep Learning-Derived Radiographic Model Performance Predicting THA

The model utilizing only the deep learning-derived radiographic variables as features had an AUROC of 0.77 and AUPRC of 0.213 (Table 6). The top two features were relevant to joint space, whereas the next three were measures of ipsilateral and contralateral hip dysplasia (FIG. 8).

Combined Model Performance Predicting THA

The combined model with baseline demographic, clinical, and radiographic variables as features had the best performance among the models with an AUROC of 0.81 and AUPRC of 0.28 (Table 6). The top two features were radiographic measurement variables. The next three were patient-reported ipsilateral hip pain, contralateral LCEA (radiographic), and analgesics use within 30 days from the baseline visit (FIG. 8).

Partial Dependency Plots for Top Features

The partial dependency plots for the top features of the combined model were inspected, thereby allowing us to describe the exact mechanics of how these factors were predictive of ten-year risk of THA. These plots are provided in FIG. 9.

For minimum joint space, there was a discontinuity in risk of THA at 2.67 mm. In particular, the difference in predictive scores implied an odds ratio (OR) of 1.78 associated with moving from a minimum width of 2.77 mm to 2.57 mm. Average joint space had a discontinuity at 4.24-mm; moving from 4.34 mm to 4.14 mm was associated with an OR=1.29 for THA risk.

Ipsilateral lateral center-edge angle (LCEA) had discontinuities at 22.4° and 19.2°; moving from 23.4° to 21.4° was associated with an OR=1.45, whereas moving from 23.4° to 18.2°, OR=1.65. Contralateral LCEA had a discontinuity at 32.7°; for moving from 33.7° to 31.7°, OR=1.33. Ipsilateral Tönnis angle had a discontinuity at 10.8°; for moving from 11.8° to 9.8°, OR=1.34.

Baseline ipsilateral hip pain was associated with an OR=1.41, and baseline analgesics, OR=1.29.

Discussion

In developing the machine learning model to predict THA ten-year risk using a multi-center cohort, it was determined that the addition of clinically relevant hip radiographic measurements, which were derived using deep learning segmentation, significantly improved predictive model performance beyond using demographic and clinical information. Specifically, the combined model's AUROC-0.81 (95% CI, 0.74-0.88) and AUPRC-0.28 (95% CI, 0.22-0.28).

Prior literature has evaluated machine learning models to predict a variety of endpoints in OA populations, however, few have predicted THA or TKA risk from radiographic data. Liu et al. recently evaluated models incorporating clinical and radiographic features, reporting AUROCs between 0.79 to 0.87 for predicting TKA. [16] Tolpadi et al. determined that using MRIs with clinical and demographic data was superior to radiographs or clinical data alone in predicting TKA, especially for early OA [17]. These results are sensible, as radiographic assessments are used in decision-making around whether to proceed with arthroplasty surgery. Indeed, pelvis radiographs portray hip structural damage severity and help confirm OA diagnosis when certain pathologic features are present [1]. When patients with hip OA symptoms present with radiographic evidence of pathologic features and have failed conservative management attempts, this information allows surgeons to make informed decisions as to whether a patient would benefit from THA.

While the incorporation of deep learning-derived radiographic measurements enhances predictive performance, it also confers several benefits relative to manually classified or abstracted radiographic data. For example, it can automatically derive radiographic features that would be difficult and time consuming to measure manually. In this study, average joint space was calculated by taking widths between the acetabular sourcil and femoral head contour at every possible degree from the femoral head center to the sourcil (at a rate of ~10 seconds per image). This would be difficult to measure manually, yet the inventive model identified average joint space as a top predictive feature in predicting THA. Moreover, our GA2M modeling automates the process of combining these radiographic and other relevant clinical data into an assessment of THA risk, which could augment the decision-making and critical reasoning of clinicians facing increasing caseloads with limited time.

Furthermore, previous studies using deep learning models have directly predicted TKA from knee radiographs. As highlighted in machine learning literature, this direct image (input) to outcome (output) approach has interpretability issues given the "black box" nature of deep learning [28]. This is an important difference with our approach. Rather than leveraging a model predicting THA directly from a hip radiograph, we used deep learning only to segment landmarks on radiographs for measurements. These bone landmarks were subsequently processed to measure clinically relevant radiographic parameters, a process that was fully interpretable (FIG. 10). These measurements were then used as features for GA2M modeling, which was likewise transparent (i.e., "glass box" model) [26, 27].

In 2017, the American Academy of Orthopedic Surgeons (AAOS) published an appropriate use criteria for hip OA management, in which five criteria are used to generate an indication profile and procedural treatment recommendations [29]. Critically, four of the five appropriate use criteria were found among the combined model's top predictive features: (1) age, (2) reported pain, (3) radiographic evaluation, and (4) presence or absence of modifiable risk factors (here, analgesic use). The study frame for the data was from 2004-2015, and the AAOS guidelines were established in 2017 after expert panel review of literature. The concordance of the top features with an established evidence-based guideline suggests our model derived features predictive of THA that are emphasized and important in clinical practice.

Furthermore, our modeling found discontinuities in predicted risk, consistent with prior work and established clinical guidelines, which may enhance the ability to provide more structured, informed assessments of medium- to long-term THA risk with patients on a case-by-case basis. In a setting where surgeon expertise is not readily available, this could be particularly helpful. A minimum joint space less than 2.67-mm, average joint space less than 4.24-mm, and age greater than 68.5 years were all associated with increased ten-year THA prediction.

In particular, joint space narrowing is a characteristic feature of all OA forms regardless of etiology. A prospective study in 2005 found a baseline minimum joint space less than 2.5-mm was associated with osteoarthritis progression (OR=1.9, 95% CI: 1.2-2.9) at a 6-year follow-up [30]. Likewise, a recent international, multicenter study found patients with a lower minimum preoperative joint width experienced a higher likelihood of achieving minimal clinically importance differences (MCID) for pain and function one-year postoperatively after THA [31]. Lower minimum and average joint space may therefore be predictive of not only medium- to long-term need for THA, but also, conditional on THA, patient-reported success in terms of reduced pain and improved function. Further studies should use radiographic-derived features, such as joint space width, to predict outcomes after THA and investigate thresholds of these features associated with good outcomes, which very well may differ from those found above (which reflect typical surgeon decision-making and established clinical guidelines). Such thresholds associated with patient success in terms of surgical outcomes could uncover improved heuristics for recommending surgery.

Ipsilateral LCEA less than 22.4° was associated with an increase in likelihood of THA within 10 years, with an even greater likelihood at values less than 19.2°. There is debate as to what defines hip dysplasia using the LCEA, though generally an LCEA between 20°-25° is thought of as borderline dysplasia and less than 20° as true dysplasia [32-35].

Furthermore, a Tönnis angle greater than 10.8° was associated with an increase in likelihood of undergoing THA within 10 years, with literature citing angles exceeding 8-10° as being indicative of dysplasia [35, 36]. Hip dysplasia is a leading etiology of hip OA secondary to supraphysiologic stresses across the acetabular cartilage matrix with structural failure of the acetabular labrum as the femoral head confers high contact pressures within a smaller volumetric area of the acetabulum [37, 38]. Several observational studies have reported strong associations between hip dysplasia and the development of hip OA [32, 38]. Hip dysplasia has been demonstrated to increase risk of THA, with estimates as high as 484% compared to individuals without dysplasia in some series [32]. Therefore, it is plausible that identification of radiographic measures suggestive of dysplasia provide early insight into the long-term risk of THA. In these patients, temporizing measures, such as arthroscopic labral repair or periacetabular osteotomy, may delay progression of OA and THA need while providing acceptable clinical outcomes [39-42].

Self-reported hip pain, analgesic use, and patient age were the most important non-radiographic features in predicting THA. Joint pain is a leading manifestation of symptomatic OA; analgesic medications are used to mitigate this symptom [1]. As such, patients who present for initial evaluation in this clinical stage may be more likely to be indicated for THA if conservative measures, such as analgesic use, have failed to ameliorate symptoms. Likewise, cartilage degeneration and bone remodeling will advance with age through continued hip use; these physiologic derangements cannot be reversed [1].

Taken together, these top radiographic and non-radiographic predictive features, combined with our modeling, could provide clinician and patients information regarding risk of medium- to long-term THA, as well as which specific risk factors drive this risk, at the initial visit. This model holds value in guiding medium- to long-term surgical management plans for providers and patients with, or at risk of, hip osteoarthritis, especially those that may develop OA secondary to hip dysplasia. This model could also be applied to project the incidence of THA in a large population. However, evaluating the specific effectiveness of these uses would require future investigation in prospective studies (e.g., randomizing providing patient-surgeon pairs with information on THA risk and risk factors, and evaluating outcomes such as satisfaction, treatments, and subsequent health status).

There were several limitations. Firstly, the training data was predominantly used to study knee OA. External validation of these models with higher THA incidence is necessary. Secondly, our deep learning radiographic measurements were validated based on manual bone landmark segmentation; final measurement values were not compared against that of orthopedic surgeons or radiologists. However, the concordance of the thresholds shown in our partial dependency plots with literature-based clinical thresholds suggests their validity. Thirdly, all measurements were scaled according to previous OAI database studies [43]. A calibration marker was not present on radiographs and reported mm values should be interpreted with this in mind. Finally, an input space of 136 total variables were utilized in the best model, making its applicability challenging in clinical settings. An abbreviated version with only top features may provide more clinical value.

Hardware and Software Infrastructure Examples

The present invention may be embodied on various computing systems and/or platforms that perform actions responsive to software-based instructions. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++, Visual Basic or the like and conventional procedural programming languages, such as the "C" programming language or similar programming languages.

Aspects of the present invention may be described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

REFERENCES

[1] Katz J N, Arant K R, Loeser R F. Diagnosis and Treatment of Hip and Knee Osteoarthritis: A Review. JAMA 2021; 325(6):568-78 doi: 10.1001/jama.2020.22171.

[2] Kurtz S, Ong K, Lau E, Mowat F, Halpern M. Projections of primary and revision hip and knee arthroplasty in the United States from 2005 to 2030. J Bone Joint Surg Am 2007; 89(4):780-5 doi: 10.2106/JBJS.F.00222.

[3] Elfiky A A, Pany M J, Parikh R B, Obermeyer Z. Development and Application of a Machine Learning Approach to Assess Short-term Mortality Risk Among Patients With Cancer Starting Chemotherapy. JAMA Netw Open 2018; 1(3):e180926 doi: 10.1001/jamanetworkopen.2018.0926.

[4] Gulshan V, Peng L, Coram M, et al. Development and Validation of a Deep Learning Algorithm for Detection of Diabetic Retinopathy in Retinal Fundus Photographs. JAMA 2016; 316(22):2402-10 doi: 10.1001/jama.2016.17216.

[5] Fontana M A, Lyman S, Sarker G K, Padgett D E, MacLean C H. Can Machine Learning Algorithms Predict Which Patients Will Achieve Minimally Clinically Important Differences From Total Joint Arthroplasty? Clin Orthop Relat Res 2019; 477(6): 1267-79 doi: 10.1097/CORR.0000000000000687.

[6] Ramkumar P N, Karnuta J M, Navarro S M, et al. Deep Learning Preoperatively Predicts Value Metrics for Primary Total Knee Arthroplasty: Development and Validation of an Artificial Neural Network Model. J Arthroplasty 2019; 34(10):2220-27 e1 doi: 10.1016/j.arth.2019.05.034.

[7] Rouzrokh P, Wyles C C, Philbrick K A, et al. A Deep Learning Tool for Automated Radiographic Measurement of Acetabular Component Inclination and Version After Total Hip Arthroplasty. J Arthroplasty 2021; 36(7):2510-17 e6 doi: 10.1016/j.arth.2021.02.026.

[8] Karnuta J M, Haeberle H S, Luu B C, et al. Artificial Intelligence to Identify Arthroplasty Implants From Radiographs of the Hip. J Arthroplasty 2021; 36(7S): S290-S94 e1 doi: 10.1016/j.arth.2020.11.015.

[9] Kunze K N, Orr M, Krebs V, Bhandari M, Piuzzi N S. Potential benefits, unintended consequences, and future roles of artificial intelligence in orthopaedic surgery research: a call to emphasize data quality and indications. Bone Jt Open 2022; 3(1):93-97 doi: 10.1302/2633-1462.31.BJO-2021-0123.R1.

[10] Anakwe R E, Jenkins P J, Moran M. Predicting dissatisfaction after total hip arthroplasty: a study of 850 patients. J Arthroplasty 2011; 26(2):209-13 doi: 10.1016/j.arth.2010.03.013.

[11] Pincus D, Jenkinson R, Paterson M, Leroux T, Ravi B. Association Between Surgical Approach and Major Surgical Complications in Patients Undergoing Total Hip Arthroplasty. JAMA 2020; 323(11):1070-76 doi: 10.1001/jama.2020.0785.

[12] Chen A, Paxton L, Zheng X, et al. Association of Sex With Risk of 2-Year Revision Among Patients Undergoing Total Hip Arthroplasty. JAMA Netw Open 2021; 4(6):e2110687 doi: 10.1001/jamanetworkopen.2021.10687.

[13] Januel J M, Chen G, Ruffieux C, et al. Symptomatic in-hospital deep vein thrombosis and pulmonary embolism following hip and knee arthroplasty among patients receiving recommended prophylaxis: a systematic review. JAMA 2012; 307(3):294-303 doi: 10.1001/jama.2011.2029.

[14] Colas S, Collin C, Piriou P, Zureik M. Association Between Total Hip Replacement Characteristics and 3-Year Prosthetic Survivorship: A Population-Based Study. JAMA Surg 2015; 150(10):979-88 doi: 10.1001/jamasurg.2015.1325.

[15] Kunze K N, Fontana M A, MacLean C H, Lyman S, McLawhorn A S. Defining the Patient Acceptable Symptom State for the HOOS J R and KOOS J R After Primary Total Joint Arthroplasty. J Bone Joint Surg Am 2022; 104(4):345-52 doi: 10.2106/JBJS.21.00550.

[16] Liu Q, Chu H, LaValley M P, et al. Prediction models for the risk of total knee replacement: development and validation using data from multicentre cohort studies. The Lancet Rheumatology 2022; 4(2):e125-e34 doi: https://doi.org/10.1016/S2665-9913(21)00324-6.

[17] Tolpadi A A, Lee J J, Pedoia V, Majumdar S. Deep Learning Predicts Total Knee Replacement from Magnetic Resonance Images. Sci Rep 2020; 10(1):6371 doi: 10.1038/s41598-020-63395-9.

[18] Tiulpin A, Klein S, Bierma-Zeinstra S M A, et al. Multimodal Machine Learning-based Knee Osteoarthritis Progression Prediction from Plain Radiographs and Clinical Data. Sci Rep 2019; 9(1):20038 doi: 10.1038/s41598-019-56527-3.

[19] Jamshidi A, Pelletier J P, Labbe A, Abram F, Martel-Pelletier J, Droit A. Machine Learning-Based Individualized Survival Prediction Model for Total Knee Replacement in Osteoarthritis: Data From the Osteoarthritis Initiative. Arthritis Care Res (Hoboken) 2021; 73(10): 1518-27 doi: 10.1002/acr.24601.

[20] Hartnett D A, Brodeur P G, Kosinski L R, Cruz A I, Jr., Gil J A, Cohen E M. Socioeconomic Disparities in the Utilization of Total Hip Arthroplasty. *J Arthroplasty*. February 2022; 37(2):213-218 e1. doi:10.1016/j.arth.2021.10.021.

[21] Sanders T L, Maradit Kremers H, Schleck C D, Larson D R, Berry D J. Subsequent Total Joint Arthroplasty After Primary Total Knee or Hip Arthroplasty: A 40-Year Population-Based Study. J Bone Joint Surg Am 2017; 99(5): 396-401 doi: 10.2106/JBJS.16.00499.

[22] Philippon M J, Briggs K K, Carlisle J C, Patterson D C. Joint space predicts THA after hip arthroscopy in patients 50 years and older. Clin Orthop Relat Res 2013; 471(8): 2492-6 doi: 10.1007/s11999-012-2779-4.

[23] Mannava S, Geeslin A G, Frangiamore S J, et al. Comprehensive Clinical Evaluation of Femoroacetabular Impingement: Part 2, Plain Radiography. Arthrosc Tech 2017; 6(5):e2003-e09 doi: 10.1016/j.eats.2017.06.011.

[24] Murray K J, Azari M F. Leg length discrepancy and osteoarthritis in the knee, hip and lumbar spine. J Can Chiropr Assoc 2015; 59(3):226-37

[25] Jang S J, Kunze K N, Vigdorchik J M, Jerabek S A, Mayman D J, Sculco P K. Deep Learning Prediction of Hip Joint Center on Standard Pelvis Radiographs. J Arthroplasty 2022 doi: 10.1016/j.arth.2022.03.033.

[26] Lou Y, Caruana R, Gehrke J, Hooker G. Accurate Intelligible Models with Pairwise Interactions. 19th Acm Sigkdd International Conference on Knowledge Discovery and Data Mining (Kdd'13) 2013:623-31 doi: Doi 10.1145/2487575.2487579.

[27] Caruana R, Lou Y, Gehrke J, Koch P, Sturm M, Elhadad N. Intelligible Models for HealthCare: Predicting Pneumonia Risk and Hospital 30-day Readmission. Kdd'15: Proceedings of the 21st Acm Sigkdd International Conference on Knowledge Discovery and Data Mining 2015: 1721-30 doi: 10.1145/2783258.2788613.

[28] Rudin C. Stop explaining black box machine learning models for high stakes decisions and use interpretable models instead. Nature Machine Intelligence 2019; 1(5): 206-15 doi: 10.1038/s42256-019-0048-x.

[29] The American Academy of Orthopaedic Surgeons. Appropriate Use Criteria: Osteoarthritis of the Hip: Management (2017). Secondary Appropriate Use Criteria: Osteoarthritis of the Hip: Management (2017) 2017. https://www.orthoguidelines.org/go/auc/auc.cfm?au-c_id=225000.

[30] Reijman M, Hazes J M, Pols H A, Bernsen R M, Koes B W, Bierma-Zeinstra S M. Role of radiography in predicting progression of osteoarthritis of the hip: prospective cohort study. BMJ 2005; 330(7501):1183 doi: 10.1136/bmj.38442.457488.8F.

[31] Rojanasopondist P, Galea V P, Connelly J W, et al. What Preoperative Factors are Associated With Not Achieving a Minimum Clinically Important Difference After THA? Findings from an International Multicenter Study. Clin Orthop Relat Res 2019; 477(6): 1301-12 doi: 10.1097/CORR.0000000000000667.

[32] Saberi Hosnijeh F, Zuiderwijk M E, Versteeg M, et al. Cam Deformity and Acetabular Dysplasia as Risk Factors for Hip Osteoarthritis. Arthritis Rheumatol 2017; 69(1): 86-93 doi: 10.1002/art.39929.

[33] Kunze K N, Alter T D, Newhouse A C, Bessa F S, Williams J C, Nho S J. Association Between Orientation and Magnitude of Femoral Torsion and Propensity for Clinically Meaningful Improvement After Hip Arthroscopy for Femoroacetabular Impingement Syndrome: A Computed Tomography Analysis. Am J Sports Med 2021; 49(9):2466-74 doi: 10.1177/03635465211021610.

[34] Kracutler M J, Safran M R, Scillia A J, Ayeni O R, Garabekyan T, Mei-Dan O. A Contemporary Look at the Evaluation and Treatment of Adult Borderline and Frank Hip Dysplasia. Am J Sports Med 2020; 48(9):2314-23 doi: 10.1177/0363546519881411.

[35] Wyles C C, Heidenreich M J, Jeng J, Larson D R, Trousdale R T, Sierra R J. The John Charnley Award: Redefining the Natural History of Osteoarthritis in Patients With Hip Dysplasia and Impingement. Clin Orthop Relat Res 2017; 475(2):336-50 doi: 10.1007/s11999-016-4815-2.

[36] Clohisy J C, Carlisle J C, Beaule P E, et al. A systematic approach to the plain radiographic evaluation of the young adult hip. J Bone Joint Surg Am 2008; 90 Suppl 4:47-66 doi: 10.2106/JBJS.H.00756.

[37] Gala L, Clohisy J C, Beaule P E. Hip Dysplasia in the Young Adult. J Bone Joint Surg Am 2016; 98(1):63-73 doi: 10.2106/JBJS.O.00109.

[38] Hernandez P A, Wells J, Usheva E, et al. Early-Onset Osteoarthritis originates at the chondrocyte level in Hip Dysplasia. Sci Rep 2020; 10(1):627 doi: 10.1038/s41598-020-57431-x.

[39] Gray B L, Stambough J B, Baca G R, Schoenecker P L, Clohisy J C. Comparison of contemporary periacetabular osteotomy for hip dysplasia with total hip arthroplasty for hip osteoarthritis. Bone Joint J 2015; 97-B(10):1322-7 doi: 10.1302/0301-620X.97B10.35741.

[40] Lerch T D, Steppacher S D, Liechti E F, Tannast M, Siebenrock K A. One-third of Hips After Periacetabular Osteotomy Survive 30 Years With Good Clinical Results, No Progression of Arthritis, or Conversion to THA. Clin Orthop Relat Res 2017; 475(4): 1154-68 doi: 10.1007/s11999-016-5169-5.

[41] Beck E C, Drager J, Nwachukwu B U, et al. Patients With Borderline Hip Dysplasia Achieve Clinically Significant Improvement After Arthroscopic Femoroacetabular Impingement Surgery: A Case-Control Study With a Minimum 5-Year Follow-up. Am J Sports Med 2020; 48(7):1616-24 doi: 10.1177/0363546520916473.

[42] Jimenez A E, Monahan P F, Miecznikowski K B, et al. Achieving Successful Outcomes in High-Level Athletes With Borderline Hip Dysplasia Undergoing Hip Arthroscopy With Capsular Plication and Labral Preservation: A Propensity-Matched Controlled Study. Am J Sports Med 2021; 49(9):2447-56 doi: 10.1177/03635465211021001.

[43] Ratzlaff C, Van Wyngaarden C, Duryea J. Location-specific hip joint space width for progression of hip osteoarthritis—data from the osteoarthritis initiative. Osteoarthritis Cartilage 2014; 22(10):1481-7 doi: 10.1016/j.joca.2014.05.017.

[44] Ronneberger O, Fischer P, Brox T. U-Net: Convolutional Networks for Biomedical Image Segmentation. Springer International Publishing; 2015:234-241.

[45] Zou K H, Warfield S K, Bharatha A, et al. Statistical validation of image segmentation quality based on a spatial overlap index. *Acad Radiol.* February 2004; 11(2): 178-89. doi:10.1016/s1076-6332(03)00671-8.
[46] Pizer S M, Amburn E P, Austin J D, et al. Adaptive histogram equalization and its variations. *Computer Vision, Graphics, and Image Processing.* 1987/09/01/ 1987; 39(3):355-368. doi:https://doi.org/10.1016/S0734-189X(87)80186-X.
[47] Tack A, Preim B, Zachow S. Fully automated Assessment of Knee Alignment from Full-Leg X-Rays employing a "YOLOv4 And Resnet Landmark regression Algorithm" (YARLA): Data from the Osteoarthritis Initiative. *Comput Methods Programs Biomed.* June 2021; 205: 106080. doi: 10.1016/j.cmpb.2021.106080.
[48] Howard J, Gugger S. Fastai: A Layered API for Deep Learning. *Information.* 2020; 11(2)doi: 10.3390/info11020108.
[49] Schwartz J T, Cho B H, Tang P, et al. Deep Learning Automates Measurement of Spinopelvic Parameters on Lateral Lumbar Radiographs. Spine (Phila Pa 1976). Jun. 15, 2021; 46(12):E671-E678. doi: 10.1097/BRS.0000000000003830.
[50] Schafer T, Krummenauer F, Mettelsiefen J, Kirschner S, Gunther K P. Social, educational, and occupational predictors of total hip replacement outcome. *Osteoarthritis Cartilage.* August 2010; 18(8): 1036-42. doi: 10.1016/j.joca.2010.05.003.
[51] Bukulmez H, Matthews A L, Sullivan C M, et al. Hip joint replacement surgery for idiopathic osteoarthritis aggregates in families. *Arthritis Res Ther.* 2006; 8(1):R25. doi: 10.1186/ar1878.
[52] Goker B, Sancak A, Arac M, Shott S, Block J A. The radiographic joint space width in clinically normal hips: effects of age, gender and physical parameters. *Osteoarthritis Cartilage.* May 2003; 11(5):328-34. doi:10.1016/s1063-4584(03)00023-2.
[53] Flecher X, Ollivier M, Argenson J N. Lower limb length and offset in total hip arthroplasty. *Orthop Traumatol Surg Res.* February 2016; 102(1 Suppl):S9-20. doi: 10.1016/j.otsr.2015.11.001.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method for determining a risk of a patient needing arthroplasty, comprising:
    acquiring demographic data for the patient;
    acquiring a medical image of a patient's anatomy, wherein the medical image depicts at least a joint of the patient;
    inputting the medical image into a first machine learning (ML) model, the first ML model configured to identify a plurality of anatomical landmarks;
    acquiring quantitative values for a plurality of anatomic measurements; and
    inputting the demographic data and the quantitative values for the plurality of anatomic measurements into a second ML machine, wherein the second ML machine is configured to output a likelihood of the patient needing arthroplasty within a time frame based on the inputted demographic data and inputted quantitative values for the plurality of anatomic measurements.

2. The method of claim 1, wherein the medical image is an AP radiograph.

3. The method of claim 1, wherein the demographic data further includes data for at least one type of demographic data from a list comprising analgesic use, patient reported pain, age, and joint stiffness.

4. The method of claim 1, wherein the plurality of anatomical landmarks includes at least a portion of a femoral head on a first side of the patient and at least a portion of an acetabulum on the first side of the patient.

5. The method of claim 4, wherein the portion of the femoral head further includes the center of the femoral head and the outer perimeter of the femoral head and the portion of the acetabulum includes an outer lateral edge of the acetabulum.

6. The method of claim 4, wherein the plurality of anatomical landmarks further includes a pelvic teardrop, an obturator foramen, a femoral trochanter, and an ischial tuberosity on the first side of the patient.

7. The method of claim 1, wherein the plurality of anatomic measurements includes one or more from the list comprising a minimum joint spacing width, an angle, and a length differential.

8. The method of claim 1, further including:
    outputting, by the first ML model, a first annotated medical image with the plurality of anatomical landmarks visually identified thereon; and
    inputting the first annotated medical image into a feature measuring module (FMM), wherein the FMM executes the step of acquiring quantitative values for the plurality of anatomic measurements.

9. The method of claim 8, further including:
    presenting the first annotated medical image with the plurality of anatomical landmarks visually identified thereon to a user on a graphic user interface; and
    providing the user with a plurality of tools to modify the plurality of anatomical landmarks on the first annotated medical image.

10. The method of claim 8, further including:
    outputting, by the FFM, a second annotated medical image with the plurality of anatomical measurements visually identified thereon;
    presenting the second annotated medical image with the plurality of anatomical measurements visually identified thereon to a user on a graphic user interface; and
    providing the user with a plurality of tools to modify the plurality of anatomical measurements on the second annotated medical image.

11. The method of claim 1, further including presenting the likelihood of the patient needing arthroplasty within the time frame to at least the patient or a user.

12. A non-transitory computer-readable medium for determining a risk of a patient needing arthroplasty, comprising instructions stored thereon, that when executed on at least one processor, cause the at least one processor to:
    acquire a medical image of the patient;
    input the medical image into a first machine learning (ML) model, the first ML model configured to identify a plurality of anatomical landmarks, wherein the plurality of anatomical landmarks includes at least a portion of a joint on a first side of the patient;

acquire quantitative values for a plurality of anatomic measurements, wherein the plurality of anatomic measurements includes a joint spacing width; and input the quantitative values for the plurality of anatomic measurements into a second ML machine, wherein the second ML machine is configured to output a likelihood of the patient needing arthroplasty within a time frame based on the inputted quantitative values for the plurality of anatomic measurements.

13. The non-transitory computer-readable medium of claim 12, wherein the instructions further cause the at least one processor to acquire demographic data for the patient, wherein the demographic data includes data corresponding to at least one type of demographic data from a list comprising analgesic use, patient reported pain, age, and joint stiffness.

14. The non-transitory computer-readable medium of claim 12, wherein the medical image depicts a portion of the femoral head and a portion of an acetabulum of the patient.

15. The non-transitory computer-readable medium of claim 12, wherein the plurality of anatomical landmarks further includes a pelvic teardrop, an obturator foramen, a femoral trochanter, and an ischial tuberosity on the first side of the patient.

16. The non-transitory computer-readable medium of claim 12, wherein the plurality of anatomic measurements further includes a hip dysplasia angle and a leg length differential.

17. The non-transitory computer-readable medium of claim 12, wherein the instructions further cause the at least one processor to:
output, by the first ML model, a first annotated medical image with the plurality of anatomical landmarks visually identified thereon;
present the first annotated medical image with the plurality of anatomical landmarks visually identified thereon to a user on a graphic user interface; and
provide the user with a plurality of tools to modify the plurality of anatomical landmarks on the first annotated medical image.

18. The non-transitory computer-readable medium of claim 17, wherein the instructions further cause the at least one processor to:
input the first annotated medical image into a feature measuring module (FMM), wherein the FMM acquire the quantitative values for the plurality of anatomic measurements;
output, by the FFM, a second annotated medical image with the plurality of anatomical measurements visually identified thereon;
present the second annotated medical image with the plurality of anatomical measurements visually identified thereon to the user on the graphic user interface; and
provide the user with a plurality of tools to modify the plurality of anatomical measurements on the second annotated medical image.

19. A system for determining a risk of a patient needing arthroplasty, comprising:
at least one processor; and
memory including instructions that, when executed by the at least one processor, cause the system to:
acquiring a medical image of the patient;
input the medical image into a first machine learning (ML) model, the first ML model configured to identify a plurality of anatomical landmarks;
acquire quantitative values for a plurality of anatomic measurements;
input the quantitative values for the plurality of anatomic measurements into a second ML machine, wherein the second ML machine is configured to output a likelihood of the patient needing arthroplasty within a time frame based on the inputted quantitative values for the plurality of anatomic measurements; and
output, by the second ML model, the likelihood of the patient needing arthroplasty within the time frame.

20. The system of claim 19, wherein the instructions further cause the system to acquire demographic data for the patient and input the demographic data into the second ML machine.

* * * * *